United States Patent [19]
Silber et al.

[11] Patent Number: 6,057,160
[45] Date of Patent: May 2, 2000

[54] METHODS FOR PREPARATION AND USE OF A COOMASSIE BRILLIANT BLUE/PROTEIN COMPLEX

[75] Inventors: Moris L. Silber, Moscow, Id.; Bruce B. Davitt, Pullman, Wash.

[73] Assignee: Washington State University Research Foundation, Pullman, Wash.

[21] Appl. No.: 09/129,974

[22] Filed: Aug. 5, 1998

Related U.S. Application Data

[60] Provisional application No. 60/054,875, Aug. 6, 1997.
[51] Int. Cl.$^7$ .......................... G01N 33/483; C07K 1/13
[52] U.S. Cl. .......................... 436/86; 436/501; 436/815; 530/391.1; 530/391.3; 530/403
[58] Field of Search .................... 436/501, 815, 436/86; 530/391.1, 391.3, 403

[56] References Cited

PUBLICATIONS

Martin et al, Oecologia, vol. 54, 205–211 (1982).
Fazekas de St. Groth et al, Biochem. Biophys. Acta, vol. 71, 377–391 (1963).
Compton et al, Analytical Biochemistry, vol. 151, 369–374 (1985).
Atherton et al, Anal. Biochem., vol. 233, 160–168 (1996).
Bradford, Anal. Biochem., vol. 72, 248–254 (1976).
Asquith et al., J. Chem. Ecology, vol. 11, 1535–1544 (1985).

Primary Examiner—Mary E. Ceperley
Attorney, Agent, or Firm—Seed Intellectual Property Law Group PLLC

[57] ABSTRACT

A rapid and simple method for making a hydrophobically associated, Coomassie Brilliant Blue (CBB) dye/protein complex comprising CBB and a protein, and a method for detecting analytes using the CBB dye/protein complex are disclosed. The method for making the CBB dye/protein complex is comprised of mixing a protein with a non-alcoholic aqueous CBB solution having a pH greater than 4, heating the mixture to a first temperature for a short pulse period, then cooling to a second temperature to form a solution containing the CBB dye/protein complex. In the method for detecting analytes that bind a CBB dye/protein complex, the analyte sample is added to the solution containing a CBB dye/protein complex to form a supernatant and a precipitate containing an analyte-bound fraction. The precipitate is dissolved in an assay solvent, and a spectral absorption of both the precipitate and supernatant is measured.

15 Claims, 18 Drawing Sheets

Supernatants, in Dark

Supernatants, in Light

METHODS FOR PREPARATION AND USE OF A COOMASSIE BRILLIANT BLUE/PROTEIN COMPLEX

CROSS-REFERENCE TO RELATED APPLICATION

This application claims the benefit of U.S. Provisional Application No. 60/054,875 filed Aug. 6, 1997.

TECHNICAL FIELD

This invention is generally directed to methods for the preparation of dye/protein complexes and use thereof for the detection of analytes, and more particularly, to the preparation of a Coomassie Brilliant Blue-BSA dye/protein complex and use thereof for the detection of tannins.

BACKGROUND OF THE INVENTION

Dye staining of proteins to form non-covalent dye/protein complexes is a method widely employed in analytical biochemistry. It is used to detect proteins in electrophoretic procedures (Fazekas de St. Groth et al., *Biochem. Biophys. Acta,* 71, 377–391, 1963), to quantify proteins (Bradford, *Anal. Biochem.,* 72, 248–254, 1976; Rinderknecht et al., *Clin. Chem. Acta,* 21, 197–203, 1968), and to detect and quantify analytes that bind to proteins (Scalbert, *Plant Polyphenols,* 259–280, 1992; Asquith and Butler, *J. Chem. Ecology,* 11, 1535–1544, 1985). A variety of dyes have been proposed and evaluated for usefulness in analytical procedures (Scalbert, 1992; Martin and Martin, *Oecologia,* 54, 205–211, 1982; Flores, *Anal. Biochem.,* 88, 605–611, 1978; Datyner and Fennimore, *Anal. Biochem.,* 55, 479–491, 1973; Atherton et al., *Anal. Biochem.,* 232, 160–168, 1996; Sohl and Splittgerber, *J. Chem. Education,* 61(3), 262–264, 1991; Compton and Jones, *Anal. Biochem.,* 151, 369–376, 1985). Two dyes with the most advantageous combination of protein specificity and sensitivity are Coomassie Brilliant Blue G-250 (CBB) (Bradford, 1976) and Remazol Brilliant Blue R (RBB) (Rinderknecht et al., 1968).

On the assumptions that (1) the detailed chemical structure of the CBB dye shown below

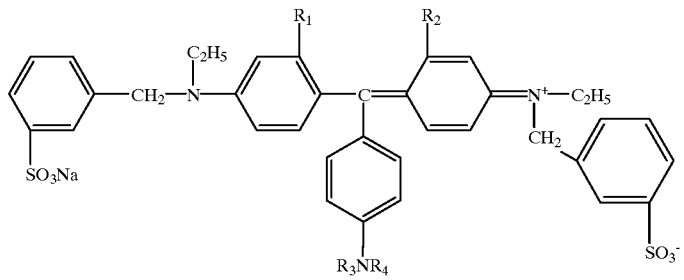

is but one of several possible resonance structures and (2) the uncharged tertiary nitrogen is equivalent to that shown carrying the positive charge, Compton and Jones (1985) suggested that the first protonation occurs at one of two tertiary amines, followed by protonation at the other. The sulfonic acid groups are less susceptible to protonation than the amino groups, due to their strong acidities (the pKa of benzosulfonic acid is 0.70).

There is good evidence that the anionic blue CBB species binds to proteins (Atherton et al., 1996; Chial and Splittgerber, 1993; Compton and Jones, 1985). At the Bradford assay pH, the dye is mostly in a highly protonated reddish form with smaller proportions of green and blue forms. The green and blue species absorb light much more intensely than the red form at the 595 nm (Chial et al., 1993), the zero-protein assay mixture has a relatively low absorbance. The lower the assay pH, the greater the proportion of the red dye species and the lower the zero-protein absorbance at 595 nm. However, the assay pH must be at the same time reasonably high so that a small proportion of the blue form remains, since it is thought to be the protein-binding species of the dye.

Addition of protein to the dye reagent of low pH results in a marked decrease of the 470 nm absorption, a new shoulder at 595 nm, and little change at 650 nm. The three different absorbance maxima of the dye reagent-protein complex correspond to the three species of dye present: the doubly protonated, positively charged red species absorbing at 470 nm, the singly protonated neutral green species at 650 nm, and the deprotonated (anion) blue dye-protein complex at 595 nm. Based on the identical absorbance maxima of the dye-protein complex and the dye anion, it was concluded (Compton and Jones, 1985) that the bound dye species is in fact in the anion form. The equilibria shown above are forced to the right as the anion is bound by protein at pH 1.0 and lower.

However, Chial and Splittgerber (1993) showed that while the blue species of CBB dye is indeed the protein-binding form, the wavelength of its maximum absorbance is different from the wavelength maximum of the dye-protein complex. The extinction coefficients of the free blue dye species and the dye-protein complex also differ. The authors concluded that these factors could allow for detection of dye-protein binding at elevated pH where the free dye is present mostly in its blue anion form. They and others (Atherton et al., 1996; Congdon et al., 1993; Splittgerber and Sohl, 1989) have observed a red shift in absorbance maximum from 585 nm for the free blue species to 620 nm for the protein-bound dye species at pH 7.0.

CBB has advantages over other proteins-staining dyes because of its exceptionally high color intensity and position of its absorption peak (Fazekas de St. Groth et al, 1963). It is advantageous over RBB in terms of specificity for proteins (Compton and Jones, 1985), sensitivity, stability, speed, convenience and economy (Atherton et al., 1996; Sohl and Splittgerber, 1991). Proteins bound to CBB bind by hydrophobic interactions that are uniform for a wide variety of proteins, and the dye/protein complex has a higher extinction coefficient at λmax than RBB dye/protein complexes. However, current methods for protein staining using CBB are disadvantageous because they denature proteins and, therefore, cannot be employed when it is important to preserve the protein in a native, functional form. Preserving the native form of stained proteins is important for some functional assays, like analyte binding or enzymatic activity. CBB methods of staining proteins are denaturing because they employ the dye in a cationic form, which typically requires the use of alcohol and acid solvents. These solvents, which tend to irreversibly denature proteins, are required to promote efficient solubilization of CBB due to its hydrophobic character, and because CBB is ordinarily used in its protonated form which has low solubility in aqueous, non-acidic and non-organic solvents. Unfortunately, there are no methods for non-covalently staining proteins with CBB that employ the dye in its deprotonated form that would be useful under non-denaturing conditions (i.e., in the absence of alcohol solvent(s) and at a pH greater than 4.0).

RBB staining methods have been employed that allow staining of some serum proteins, such as albumins, in a way that retains some functional activity of the proteins (Asquith and Butler, 1985). However, RBB has several disadvantages as a protein stain. RBB is even less soluble in aqueous media than CBB, and is a less stable stain that tends to "leak" from the protein into the solvent media, which lowers precision and reproducibility of measurements of the dye/protein complex. RBB has a lower extinction coefficient at λmax than CBB and, therefore, lower sensitivity for detecting protein. It is not as specific for proteins, and stains primarily by ionic association with positively charged amino groups on proteins and is thus less uniform than CBB. RBB is highly negatively charged at pH levels above 5.0, which tends to cause aggregation and unwanted precipitation of proteins at higher pH levels. Further, the dye itself also tends to precipitate without protein in the presence of methanolic solvents, which may be required for the preparation of some analytes. Because of these problems, the use of RBB as a protein stain, and more particularly for maling dye/protein complexes useful in detecting analytes, is more limited than CBB.

The ability of some analytes to bind non-denatured proteins is the basis for certain methods of analyte detection, including, for example, the detection of tannins. Tannin detection by protein binding employs the distinguishing characteristic of tannins to bind and precipitate proteins (Giner-Chaves, Ph.D. Thesis, Cornell University, 1996; Hagerman and Butler, *Methods in Enzymology,* 234, 429–437, 1994; Hagerman, *Phenolic Compounds in Foods and Their Effects on Health,* 236–262, 1992; Haslam, et al., Id., 8–50; Scalbert, 1992; Field and Lettinga, *Plant Polyphenols,* 673–692, 1992; Dawra et al., *Anal. Biochem.,* 132, 50–79, 1988). These methods have found wide application in biological and/or ecological studies for the detection of tannins in plant materials, feeds and foods (Hagerman, 1992; McArthur et al., *Plant Defenses Against Mammalian Herbivory,* Chap. 6, 103–114, 1991; Asquith and Butler, 1985; Mole and Waterman, *Oecologia,* 72, 137–147, 1987; Bate-Smith, *Phytochemistry,* 16, 1021–26, 1977, Hagerman and Butler, *J. Agric. Food Chem.,* 28, 944–947, 1980; Swain, *Herbivores,* 657–682, 1979; Haslam and Lilley, *Plant Flavanoids in Biology and Medicine,* 53–65, 1986; Rinderknecht et al., 1968).

Methods for detecting tannins by protein precipitation differ in the choice of protein precipitated, as well as the parameters used for evaluating the precipitation. Three protein precipitation assays have been developed in this regard: (1) hemoglobin-precipitation, the "astringency assay" (Okuda et al., *Chem. Pharm. Bull.,* 33, 1424–1433, 1985; Schultz et al., *J. Agric. Food Chem.,* 29, 823–832, 1981; Bate-Smith, *Phytochemistry,* 12, 907, 1973; *Phytochemistry* 16, 1421, 1977); (2) β-glucosidase-precipitation (Goldstein and Swain, *Phytochemistry,* 4, 185, 1965); and (3) Bovine Serum Albumin (BSA)-precipitation (Hagerman and Butler, *J. Agric. Food Chem.,* 26(4), 809–812, 1978). Unfortunately, each of these assays has disadvantages. The hemoglobin-precipitation assay is inconvenient because it requires freshly drawn blood, and because some non-tannin phenols present in plant extracts absorb at the same λmax wavelength (578 nm) used for measuring the amount of hemoglobin precipitated (Scalbert, 1992; Makkar et al., 1987; Martin and Martin, 1982). The β-glucosidase assays are based on the ability of tannins to inhibit enzyme activity and rely on measurement of residual β-glucosidase activity in a supernatant after protein precipitation in the presence of tannins (Martin and Martin, 1982; Hagerman and Butler, 1978). Such methods are cumbersome, time consuming and complicated.

The BSA-precipitation assay, originally introduced by Hagerman and Butler in 1978, is more useful because of speed and ease of use. However, the original method, and subsequent modifications thereof, have other drawbacks. As originally developed, the assay relies on direct measurement of tannins, rather than the protein in the tannin-protein complexes (Makkar et al., *Anal. Biochem.,* 166, 435–439, 1987). Nonspecific binding of other phenols to tannin-protein complexes introduces a large error into the method (Hagerman and Butler, 1978). A modification of this assay measures proteins in a redissolved precipitate by the ninhydrin reaction which has limited interference from polyphenols (Mole and Waterman, 1987). This assay requires proteins in the precipitate to be hydrolyzed with 13.5N NaOH at 120° C. before measurement of the released amino acids with ninhydrin (Makkar et al., 1987). This is technically more laborious and time consuming than direct measurement of a pre-labeled protein.

A modification that uses radioactively labeled BSA relies on measurement of the amount of radioactivity precipitated in the presence of tannins (Hagerman and Butler, 1980). Measurement of radioactive samples is expensive, requires special equipment, special expertise and trained staff. Therefore, many investigators prefer another modification that uses dye-labeled BSA (Asquith and Butler, 1985). This assay relies on covalently labeling the protein with the dye RBB, but suffers from all the disadvantages mentioned above for protein staining therewith. The disadvantages are such that an additional assay of protein determination (Lowry method) may be required to obtain reliable results. Furthermore, the assay is limited to measuring tannin-bound protein present in the precipitate and is unable to determine the amount of tannins remaining in the supernatant. This limits the accuracy of the assay and the range of tannin concentrations that can be determined because tannin precipitation of proteins strongly depends on the ratio of tannin to protein, thus some undetected tannins may remain present in the supernatant at certain tannin concentrations.

Accordingly, there is a need in the art for a simple, rapid, and economical method to make stable, dye/protein complexes using a sensitive and protein specific dye like CBB under conditions that do not irreversibly denature proteins. There is also a need to provide methods that are rapid, sensitive, reproducible, and economical for the detection of analytes, like tannins, that bind to dye/protein complexes and for an assay that allows accurate determination of tannin levels present both in a precipitate and supernatant fraction. The present invention fulfills these needs and provides other related advantages.

SUMMARY OF THE INVENTION

In brief, this invention relates to a rapid and inexpensive method for the preparation of stable, non-denatured, Coomassie Brilliant Blue (CBB) stained proteins that allows efficient association of CBB with a standard protein, such as bovine serum albumin (BSA), without the use of alcohols or acidic solvents. The method forms a dye/protein complex that preserves essential protein nativity. The complex has high spectrophotometric sensitivity and comparatively long chemical stability. The invention also relates to the use of the dye/protein complex in methods for quantitative in vitro detection of tannin analytes.

The method for making the dye/protein complex comprises a pulse heating step wherein a protein is heated to a first temperature in a non-alcoholic, aqueous dye solution of CBB for a short pulse period, then cooled to a second temperature to form a mixture containing a dye/protein complex. Optionally, the mixture may be dialyzed against a second non-alcoholic, aqueous solution to exchange solvents and/or remove unbound dye and from the mixture Excluding dialysis time, the entire method can be performed in less than 10 minutes. The protein in the dye/protein complex is not denatured and, therefore, retains essential native activities. The dye/protein complex is stable and can be stored refrigerated or at room temperature without loss of dye from the complex. The dye/proteins complex is a highly sensitive reagent that is superior to covalently labeled dye/protein complexes prepared with RBB in several properties. In addition, the method is adaptable to the preparation of a variety of dye/protein complexes.

In the practice of this invention, the method for detecting analytes that bind and precipitate the dye/protein complex comprises two steps. First, an analyte sample is added to the solution containing the dye/protein complex and mixed to form a precipitate containing an analyte-bound fraction and a supernatant containing a bound and unbound fraction. Second, the precipitate is dissolved in an assay solvent and a spectral absorption of the analyte-bound fraction is measured to quantify the dye/protein complex present in the precipitate, and the amount of dye/protein complex remaining in the supernatant is also measured to determine the unbound fraction. Quantification of the analyte concentration may then be derived from either the measurement of the precipitate alone, or in combination with the measurement of the supernatant, each of which is a function of the amount of analyte in the sample.

The method is superior to other methods for detecting tannins in that it is simple, rapid and inexpensive. It has several advantages over methods based on covalently-labeled RBB protein complexes. For example, it is more sensitive, so lower amounts of analyte may be detected because of a high extinction coefficient of the protein/dye complex and a higher dye to protein ratio in the complex. The dye/protein complex can be reliably assayed in a direct, one step measurement, without need of an additional protein measurement step. The dye/protein complex does not precipitate in the presence of methanolic solvents and thus can be used with samples extracted with methanol. Measurement of both supernatant and precipitate amounts of the dye/protein complex allows more accurate quantification over a wider range of analyte concentrations. In addition, the assay method is adaptable to the detection of a variety of analytes.

These and other aspects of this invention will be evident upon reference to the following detailed description and attached drawings. To this end, certain references are cited herein for purpose of clarity, and to provide additional supporting disclosure. Such references are each incorporated by reference in their entirety.

DETAILED DESCRIPTION OF THE INVENTION

Figure 1:
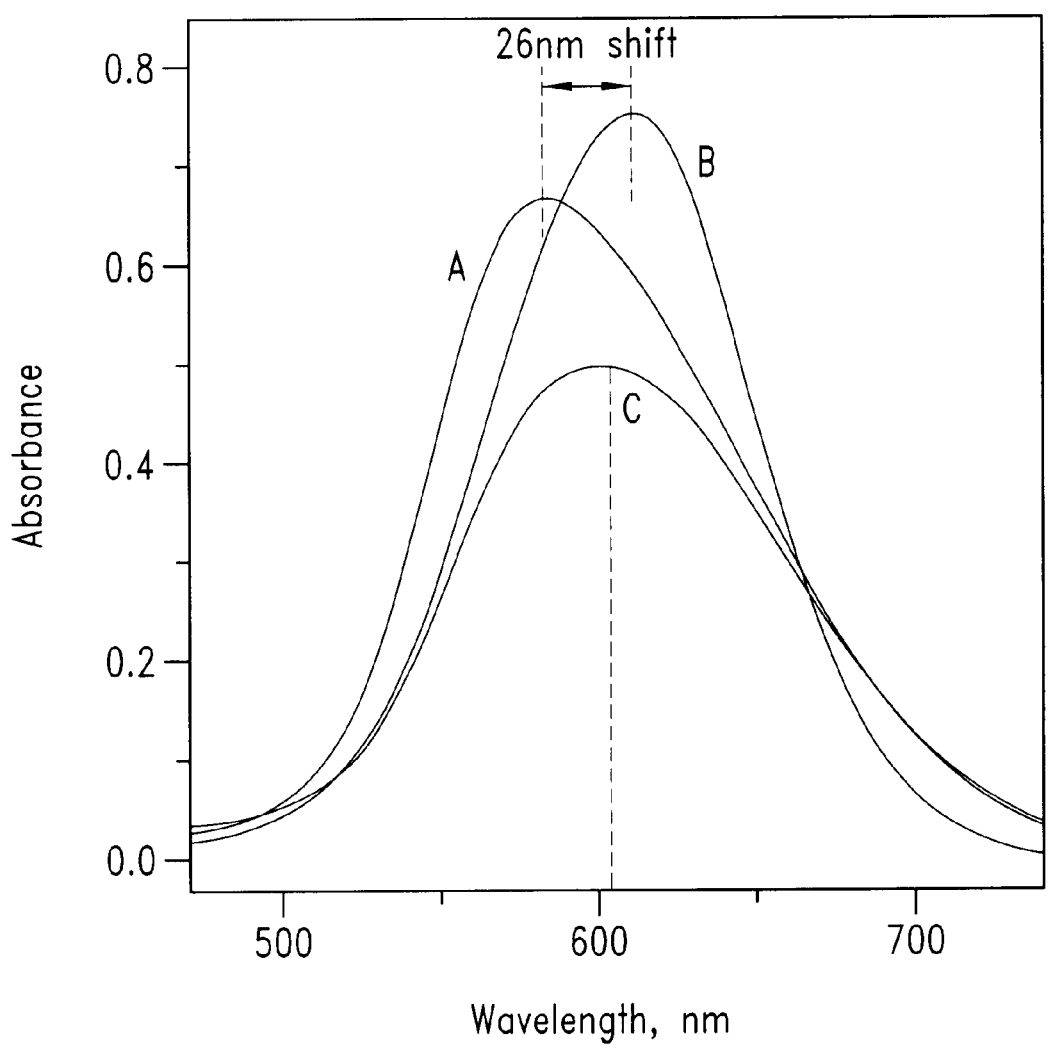
FIG. 1 illustrates absorbance spectrum profiles for CBB and a CBB-BSA dye/protein complex.

As mentioned above, the present invention is generally directed to methods for the preparation of dye/protein complexes and uses thereof for the detection of analytes, and more particularly, to the preparation of a dye/protein complex with a Coomassie Brilliant Blue (CBB) dye, and the protein bovine serum albumin (BSA), which forms a CBB-BSA dye/protein complex that may be used for the detection of analytes such as tannins.

As used herein, CBB refers to several forms of triphenylmethane dyes (sometimes known as the magenta family of dyes), which have the following structure (I):

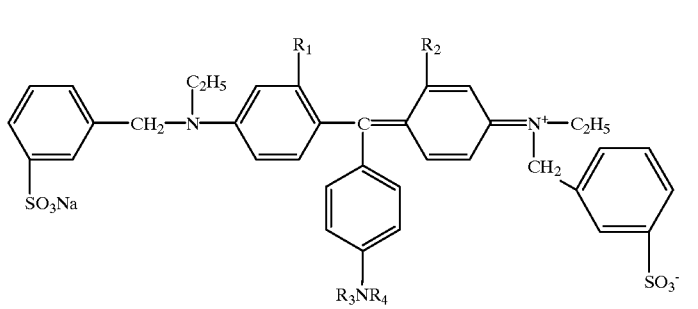

(I)

where $R_1$ and $R_2$ are the same or different and independently selected from hydrogen and $C_1$–$C_3$ alkyl, $R_3$ is selected from $C_1$–$C_6$ alkyl and substituted phenyl, and $R_4$ is selected from hydrogen and $C_1$–$C_6$ alkyl, with the proviso that $R_4$ is hydrogen when $R_3$ is a substituted phenyl.

CBB dyes of structure (I) above are commercially available from a variety of sources. While any CBB dye having the above structure may be used in the practice of this invention, in a preferred embodiment, $R_1$ and $R_2$ are each methyl, $R_3$ is p-ethoxy-phenyl and $R_4$ is hydrogen. Such a dye is commercially available from Sigma Chemical Company (St. Louis, Mo.) under the tradenames Brilliant Blue G, Coomasie Brilliant Blue G-250 or Bradford reagent. It is a violet-brown powder, soluble in hot and less in cold water (50%) and ethanol (40%). In aqueous 0.25% (w/v) solutions it is of bright-blue color.

This dye is a bright-blue compound, soluble in hot water and slightly soluble in ethanol.

One or more of the R groups of structure (I) above (i.e., $R_1$, $R_2$, $R_3$ and/or $R_4$) are capable of association with proteins at neutral pH and temperatures below 50° C., without denaturing the protein. However, conventional methods use the dye in its cationic, protonated form which is solubilized in the presence of strong protein denaturants like acids and ethanol. For example, a typical CBB staining protocol includes concentrated phosphoric acid and 95% ethanol. This results in denaturation of the protein during the formation of a CBB dye/protein complex. In the practice of this invention, the reaction can take place at pH levels above 4.0, in the absence of alcohols, and without altering the ionic strength of the protein solution. This avoids denaturation of the proteins and prevents protein aggregation that could lead to unwanted precipitation.

In the method of this invention, the dye is used in its unprotonated form, in the absence of alcohol, and at pH levels above 4.0. Under these conditions, the native properties of the stained protein may be preserved so that the dye/protein complex can be used as a reagent in subsequent methods which depend upon a native activity of the protein. In one embodiment, the native property of the protein bovine serum albumin (BSA), to bind and precipitate in the presence of tannins, is preserved after staining with CBB. In other embodiments, proteins including, but not limited to, enzymes, lectins, antibodies, antigens, binding proteins, peptide hormones, transport proteins and receptors, may also have native properties preserved after staining.

BSA is a simple protein with a relatively low molecular weight of 67,500 D. It is water soluble, easily crystallizable, and available in highly purified form. BSA contains 16% nitrogen and is widely used as a standard protein for calibration procedures. It has an excess of acidic amino acids, glutamate and aspartate (20% to 25%), which gives it a high net negative charge (pI 4.9), in solutions having a pH of about 6.0 or greater. However, at pH range of 4.0 to 5.0, which is optimal for tannin binding, BSA has a neutral to slightly positive net charge. When BSA is heated to about 100° C. in solution having a pH of about 4.5 it undergoes conformational changes and achieves a "molten globule" state. In the practice of this invention, the protein is pulse heated, which means it is briefly heated to a first temperature, then cooled to a second temperature in the presence of the dye. It is likely that favorable conformational modifications in the BSA molecule occur during the pulse-heat treatment because the method results in a dye/protein complex having a high dye to protein ratio (1 to 7.25). After the pulse heat treatment, the BSA retains its native properties.

The method of this invention for making the dye/protein complex comprises a pulse heating step, which means heating and cooling a mixture within a brief pulse period of time. A non-alcoholic, aqueous solution of CBB having a pH greater than 4.0, is mixed with a protein and pulse-heated to a first temperature for a short pulse period, then cooled to a second temperature that is less than the first temperature to form a mixture containing the dye/protein complex. The first temperature may be between 0° C. and 120° C., preferably room temperature to 120° C., more preferably 90° C. to 110° C., and most preferably 100° C. The pulse period may be for any period greater than 0 seconds, preferably 3 minutes. The second temperature may be any temperature greater than 0° C. and less than 120° C., preferably room temperature. The aqueous solution of CBB may be prepared in many ways, but a particularly rapid way to dissolve CBB is by quickly heating to 100° C. for 3 minutes.

The dye/protein mixture may be further treated as needed for a given procedure, for example, buffer exchange and/or removal of excess dye may be done by dialysis. In the case of a dye/protein mixture comprising a CBB-BSA dye/protein complex to be used for the detection of tannins, the dye/protein mixture is pulse heated for 3 minutes in a first non-alcoholic solution comprised of about 1% NaHCO3, pH 8.2. After pulse heating, the dye/protein mixture solution is dialyzed against a second, non-alcoholic, aqueous solution of about 0.2M acetate at H 5.0, which exchanges the first solution for the second solution which is more suitable for tannin binding. Dialysis also may remove any unbound dye that might remain in the dye/protein mixture after pulse heating.

A spectral absorption of the solution containing the dye/protein complex may be measured to quantify and characterize the dye/protein complex. Other measurements may also be taken for further characterization of the dye/protein complex, such as measurements of functional activity of the protein in the dye/protein complex, measurements of pH affects and measurements of stability of the dye/protein complex.

FIG. 1 shows an absorbance spectrum for a dye/protein complex prepared according to this invention using CBB G-250 as the dye and BSA as the protein. Spectrum A shows the absorbance of CBB in a first non-alcoholic aqueous solution comprised of 0.2M acetate buffer, pH 5.0. The spectrum has a $\lambda$max of 582 nm with an extinction coefficient, $\epsilon=4.5\times10^4$ L mol$^{-1}$cm$^{-1}$. Spectrum B shows the absorbance of CBB in dehydrated ethanol. The $\lambda$max is shifted to 608 nm and has an extinction coefficient $\epsilon=1.39\times10^4$ L mol$^{-1}$cm$^{-1}$. This shift in $\lambda$max is characteristic of CBB in a hydrophobic medium. Spectrum C shows the absorbance of the CBB-BSA dye/protein complex in 0.2M acetate buffer, pH 5.0. It has a $\lambda$max of 602 nm and an extinction coefficient $\epsilon=5.8\times10^4$ L mol$^{-1}$cm$^{-1}$. The intermediate $\lambda$max in the aqueous solution indicates that CBB is bound to BSA by hydrophobic association. The extinction coefficient of the complex is 5.4 fold greater than that of BSA covalently stained with the dye RBB.

Figure 2:
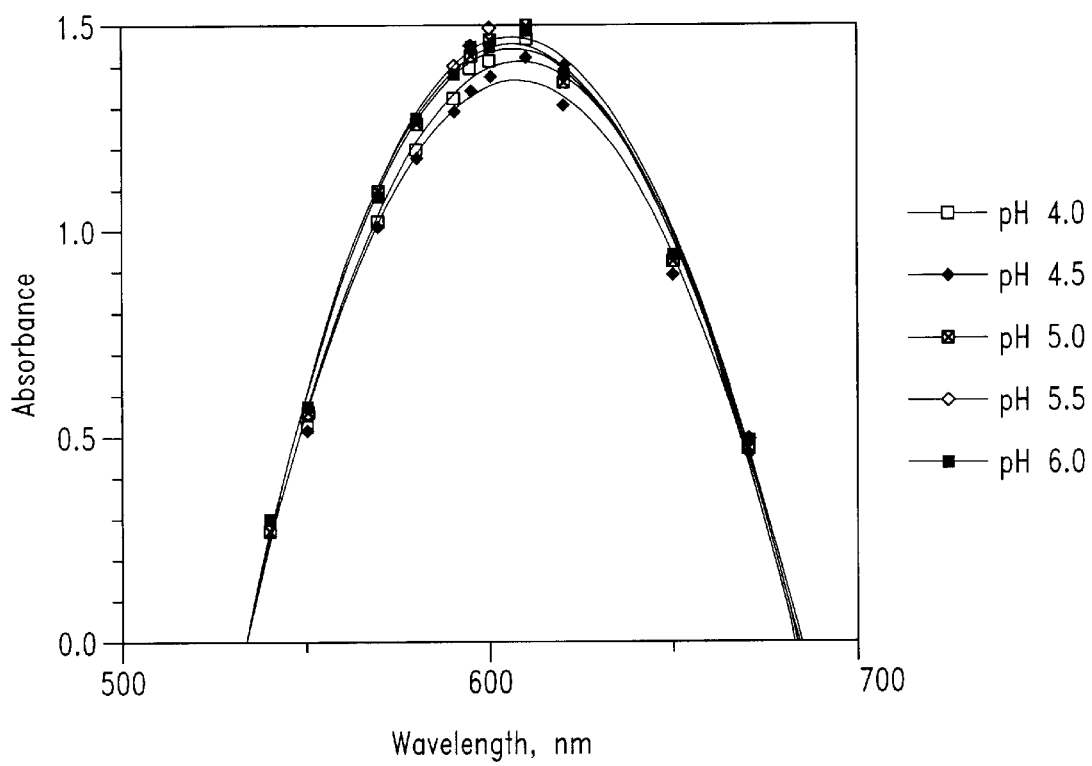
FIG. 2 illustrates the effect of pH on the absorbance spectrum of the CBB-BSA dye/protein complex.

FIG. 2 shows an effect of pH on the absorption of the CBB-BSA dye/protein complex. There is little change in the absorption spectrum within a pH range from 4.0 to 6.0 which is a preferred pH range for the detection of tannins by precipitation. This indicates that the dye/protein complex can be effectively detected at least within this pH range without loss of sensitivity. Hydrophobic interactions are known to be independent of pH, therefore, the effective pH range of stability for the CBB-BSA dye/protein complex or other dye/protein complexes prepared by this invention may well exceed the limits of the range depicted in FIG. 2.

Figure 3:
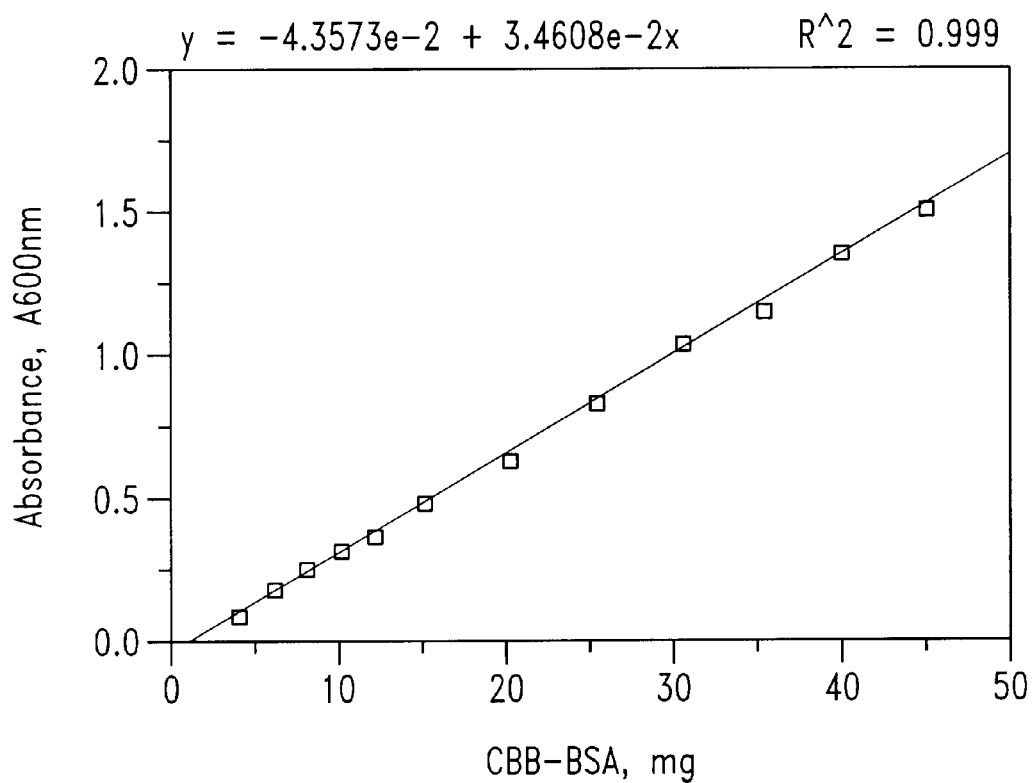
FIG. 3 illustrates concentration dependence for the spectral absorbance of the CBB-BSA dye/protein complex at $\lambda$max.

FIG. 3 shows a concentration dependence for the absorbance of the CBB-BSA dye/protein complex. The absorbance as a function of anion CBB-BSA concentration follows the Lambert-Beer law over the range of concentrations from at least 0.5 to 25 mg ml$^{-1}$ ($7.3\times10^{-3}$M to $3.6\times10^{-1}$M) with a polynomial regression curve with R^2=0.993 for the concentrations of BSA tested. The linear absorbance over the broad range of concentrations illustrates that the CBB-BSA dye/protein complex can be accurately quantified in a variety of applications that may require use of CBB-BSA at any of a wide range of concentrations.

Figure 4:
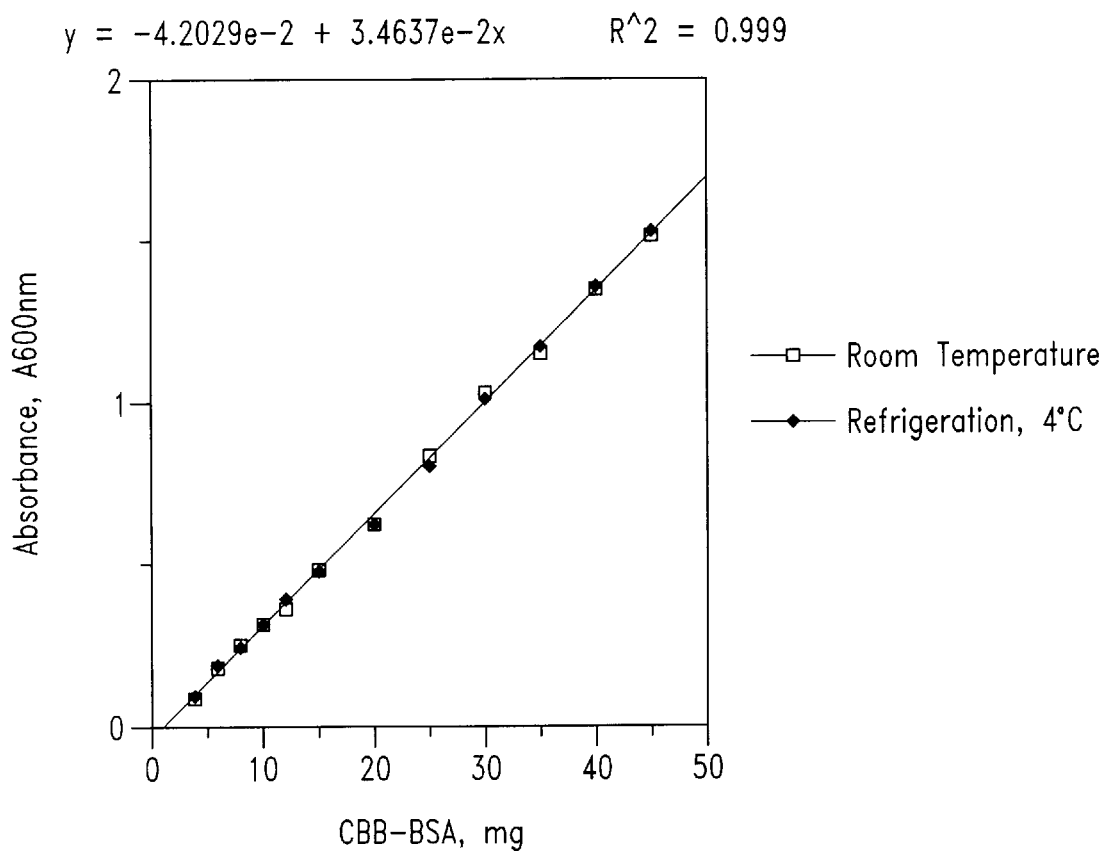
FIG. 4 illustrates stability of the CBB-BSA dye/protein complex after 26 days storage at two different temperatures.

FIG. 4 shows a stability of the CBB-BSA dye/protein complex after 26 days storage at two different temperatures (i.e., 4° C. and room temperature). There is no significant loss of absorbance or linearity after 26 days of storage and no difference in stability for storage at 4° C. or room temperature, indicating the CBB-BSA dye/protein complex is stable for at least 26 days.

While this invention has been illustrated in the context of a dye/protein complex using the G-250 form of CBB and the protein BSA, other embodiments of this invention may include other forms of CBB according to structure (I). Other proteins may also be used provided that they are not irreversibly denatured upon pulse heat treatment in the presence of the dye at pH levels greater than 4.0. Similarly, the invention allows the temperatures used, as well as the pulse period, to be selected according to the particular dye/protein complex being prepared. These parameters can be quickly determined in the practice of this invention by simply pulse heating a dye and a protein to various heating and cooling temperatures, then measuring a specific functional activity of the protein. The combination of temperatures and dyes giving the most suitable activity can then be selected.

A general method of this invention for detecting an analyte that binds to a dye/protein complex comprises two steps. First, the analyte is added to the solution containing a dye/protein complex and mixed for a period of time necessary to form an equilibrated mixture containing an analyte-bound fraction and unbound fraction of the dye/protein complex. Second, the analyte is detected by an assay of the dye/protein complex present in the analyte-bound fraction or more preferably, by an assay of the dye/protein complex present in both, the analyte-bound fraction and the unbound fraction.

The analyte may be any species that binds to the dye/protein complex, preferably a species that forms a precipitate of the dye/protein complex, and more preferably a tannin. The assay may be any method for specifically detecting dye/protein complex in any fraction. In a preferred embodiment, the analyte-bound fraction forms a precipitate containing the dye/protein complex which can be dissolved in an assay buffer, while the unbound fraction remains in a supernatant, in equilibrium with unprecipitated dye/protein complex, and the amount of dye/protein complex present in both the precipitate and the supernatant may be assayed by spectrophotometric measurement.

In a method representing one embodiment of the invention, a sample containing tannins is added to a solution containing a CBB-BSA dye/protein complex. The analyte-bound fraction forms a precipitate which may be collected by centrifugation, filtration or other conventional method. The precipitate is dissolved in an assay solvent containing sodium dodecyl sulfate (SDS), triethanolirnine, and acetate buffer, pH 5.0 and the spectral absorption of the resulting solution is measured at 600 nm.

Figure 5:
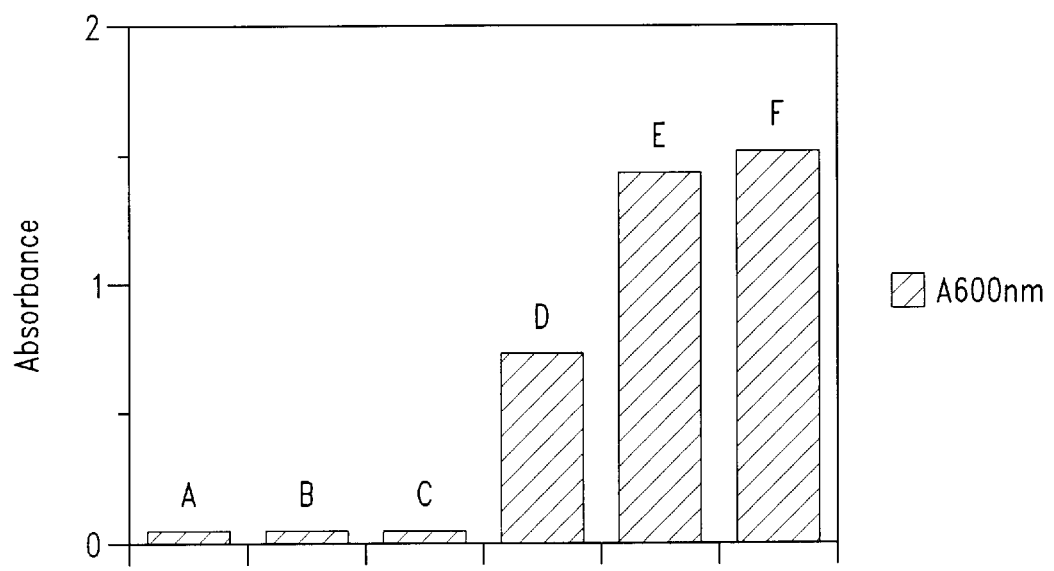
FIG. 5 illustrates tannin detection by precipitation of the CBB-BSA dye/protein complex in a methanolic solution containing tannins.

In this method of tannin quantification only the amount of CBB-BSA present in the precipitate is determined. Samples containing tannins of unknown concentration are mixed with a fixed amount of CBB-BSA ($N_o$) and stirred until a precipitate forms. The precipitate is dissolved and a spectral absorbance is measured to quantify the amount of CBB-BSA in the precipitate. Quantification of the unknown concentration of tannins ($S_0$) is estimated by interpolation from the amount of CBB-BSA precipitated by the unknown sample, using standard curves for CBB-BSA precipitation calibrated using known quantities of tannins. As shown in FIG. 5, CBB-BSA precipitation may be roughly proportionate to tannin concentration when $S_0$ for the tannins is within a certain range of concentrations.

FIG. 5, panels A–C, also shows that the CBB-BSA dye/protein complex does not form a precipitate in the presence of 50% methanol in the absence of tannins. This contrasts with the known tendency of methanol to precipitate BSA covalently labeled with the dye RBB. Panels D–F show that the CBB-BSA dye/protein complex is precipitated in different amounts according to the amount of tannin added to the mixture. Other tests show that the range of tannin concentrations detectable is wide. The CBB-BSA dye/protein complex is highly soluble, so high amounts of the CBB-BSA dye/protein complex may be used (e.g., 45 mg) for detecting high amounts of tannin. Conversely, the CBB-BSA dye/protein complex is highly sensitive thus, low amounts of the CBB-BSA dye/protein complex can be used to detect lower amounts of tannin.

Figure 6:
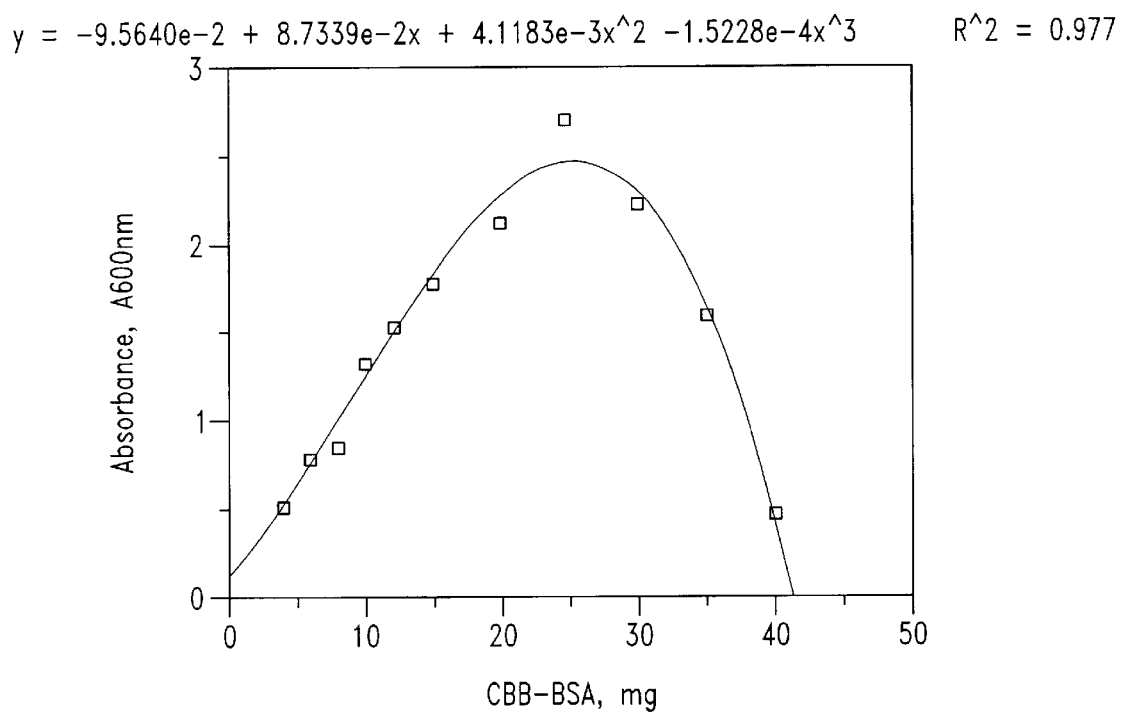
FIG. 6 illustrates protein concentration dependence for the precipitation of the CBB-BSA dye/protein complex by tannins.

It is known in the art that tannin precipitation of proteins strongly depends on the ratio of protein to tannins in solution, and on the type of tannins present. FIG. 6 shows that the method of this invention exhibits the same properties. For a fixed amount of tannin, the precipitation of the CBB-BSA dye/protein complex follows a bell shaped curve with respect to the amount of the CBB-BSA dye/protein complex present in the solution as is expected for precipitation that depends on the ratio of protein to tannin. This characteristic allows tannins to be more accurately determined quantitatively by another, preferred embodiment of the method of this invention, rather than the method described above.

The above method works when $S_0$ falls within a range that is greater than a critical concentration (l) necessary to form a precipitate with the fixed amount of CBB-BSA ($N_o$), and less than a limit amount (L), at which no more CBB-BSA remains in solution. When $S_0$ is greater than L there will be some undetected tannin remaining in the supernatant so quantification may be inaccurate. In other words, when $N_o$ is low relative to $S_0$, the amount of precipitated CBB-BSA will be proportionate to $S_0$, but when $N_o$ is high relative to $S_0$, there will not be sufficient tannins per CBB-BSA molecule to form the critical amount of binding necessary to cause precipitation. In the later case, tannins remaining in the precipitate will go undetected by the above method. This limitation stems from the fact that protein precipitation by tannins is dependent on the ratio of $S_0$ to $N_o$ which has been a major problem in conventional methods of tannin detection that rely on measurement of a precipitate only.

This problem is overcome in a preferred method of this invention for tannin detection whereby the total tannin concentration is determined by measurements of the CBB-BSA present both in the precipitate and in the supernatant. Because the CBB-BSA dye/protein complex formed by this invention remains stable in solution, even in the presence of methanol, the amount of CBB-BSA in the supernatant can be reliably measured after the precipitation. By combining measurements of both the amounts of CBB-BSA precipitated and the amount in the supernatant, tannin concentrations can be determined over a wider range of $S_0$ values than in the simple method. In this preferred method, varying amounts of the CBB-BSA dye/protein complex are added to a fixed amount of the tannin sample of unknown concentration $S_0$. As in the above method, a spectral absorbance representing the amount of CBB-BSA in the precipitate is measured ($OD_p$), as well as the amount remaining in the supernatant ($OD_s$). The values representing $OD_p$ and $1/OD_s$ may then be graphically plotted to form two curves, or fit to polynomial expressions of two curves of best fit. The point where the two curves intersect, i.e., where $OD_p$ is equal to $1/OD_s$ is a unique value characteristic of a given tannin concentration. The $S_0$ for an unknown sample may then be determined by interpolation from a set of intersection points obtained from calibration standards representing known concentrations of tannins. This allows accurate determination of the $S_0$ regardless of dependence on the dye to protein ratio. This method is illustrated further by the following theoretical calculations and empirical observations of precipitate formation in the case where precipitate formation is dependent on a ratio of $S_0$ to $N_o$.

Substrate molecules (tannin, etc.) (S) cause the precipitation of CBB-BSA dye/protein molecules (N) when the number of substrate molecules hydrophobically linked to the dye/protein molecule exceed critical value l. Consider first, an equilibrium between N and S molecules binding to form a combined molecule (C).

$$N + S \xrightleftharpoons{K} C \tag{1}$$

Assuming that each protein (BSA) molecule has $m_{max}$ adsorption sites, one has in the case of Langmuir type of adsorption:

$$\overline{m} = m_{max}\frac{KS}{1+KS} = m_{max}\frac{K(S_0 - \overline{m}N_0)}{1+K(S_0 - \overline{m}N_0)} \tag{2}$$

where K is adsorption equilibrium constant, $\overline{m}$ is the average number of adsorption sites occupied by substrate molecules in a protein molecule.

From Equation (2) it can be derived that $$\overline{m} = \frac{m_{max}N_0 + S_0 + K^{-1} - \sqrt{(m_{max}N_0 + S_0 + K^{-1})^2 - 4m_{max}N_0 S_0}}{2N_0} \tag{3}$$

Assuming Poisson distribution for substrate molecules distribution over proteins, $$P(k) = e^{-\overline{m}}\frac{(\overline{m})^k}{k!} \tag{4}$$

it can be seen that the portion of CBB-BSA molecules that have more than l linked substrate molecules, and hence are in the precipitate, is equal to $$\prod = \sum_{k=l}^{\infty} P(k) = \sum_{k=l}^{\infty} e^{-\overline{m}}\frac{(\overline{m})^k}{k!} \tag{5}$$

The optical density of CBB-BSA in the precipitate ($OD_p$) is $$OD_p = \varepsilon * \prod * N_0 \tag{6}$$

or $$OD_p = \varepsilon N_0 \sum_{k=l}^{\infty} e^{-\overline{m}}\frac{(\overline{m})^k}{k!} \tag{7}$$

Given a total optical density of the added CBB-BSA as OD, the optical density of CBB-BSA in solution ($OD_s$) is:

$$OD_s = OD - OD_p \tag{8}$$

or $$OD_s = \varepsilon N_0 \sum_{k=0}^{l} e^{-\overline{m}}\frac{(\overline{m})^k}{k!} \tag{9}$$

Both $OD_p$ and $OD_s$ dependencies on $N_0$ can be numerically calculated using these equations, and the effect of increasing concentrations of CBB-BSA on substrate precipitation can be theoretically evaluated. By assuming initial concentrations of CBB-BSA ($N_0$), substrate ($S_0$), average number of adsorption sites (m), critical number of adsorption sites (l), and equilibrium constant (K), theoretical curves can be generated representing the optical density values for $OD_p$ (precipitate absorbance) and $1/OD_s$ (supernatant inverse absorbance).

Figure 7:
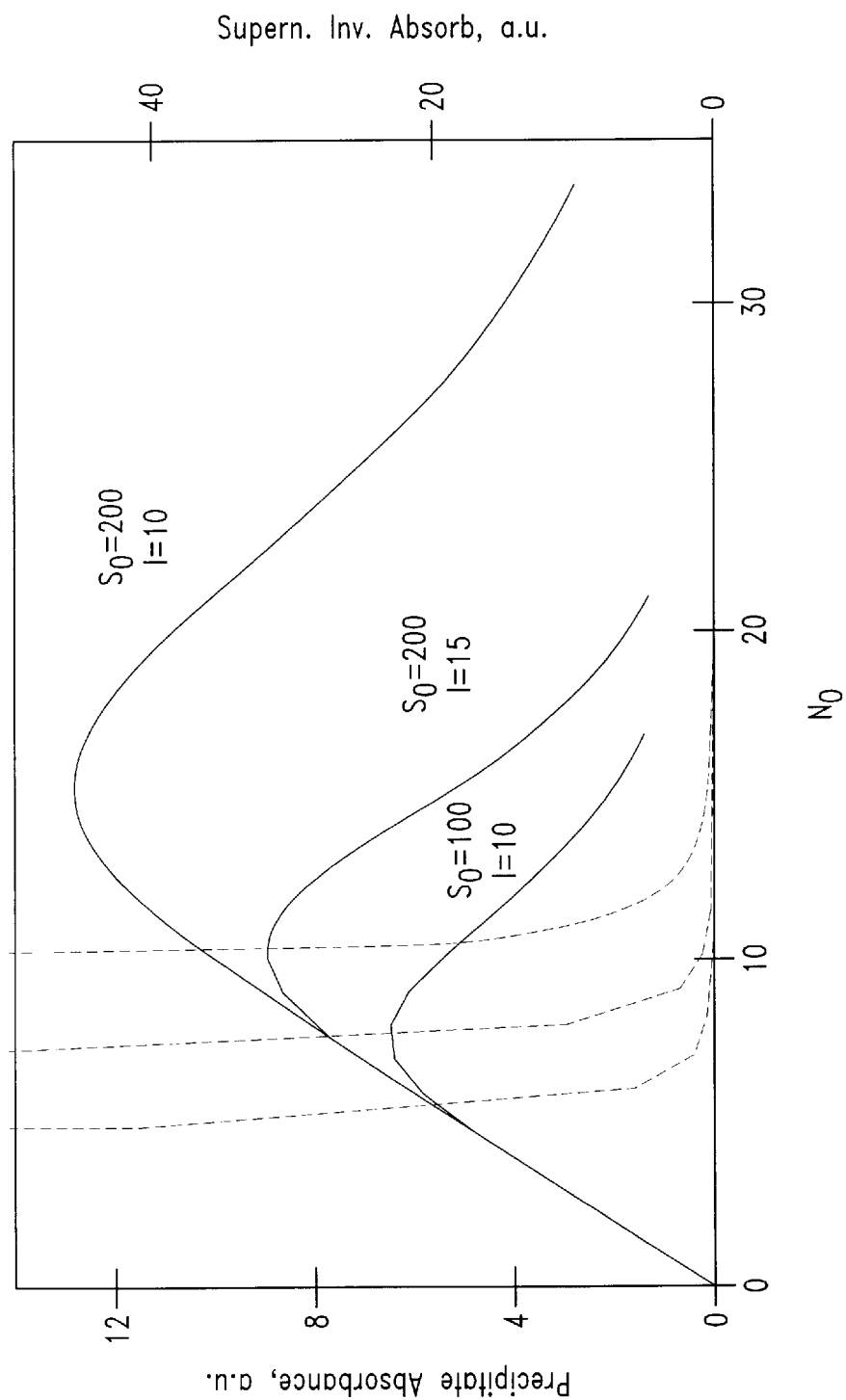
FIG. 7 illustrates theoretical dependence of an intercept point between precipitate and inverse supernatant curves for analytes present at two arbitrary $S_0$ values (100 and 200), or having two arbitrary l values (10 and 15).
Figure 8:
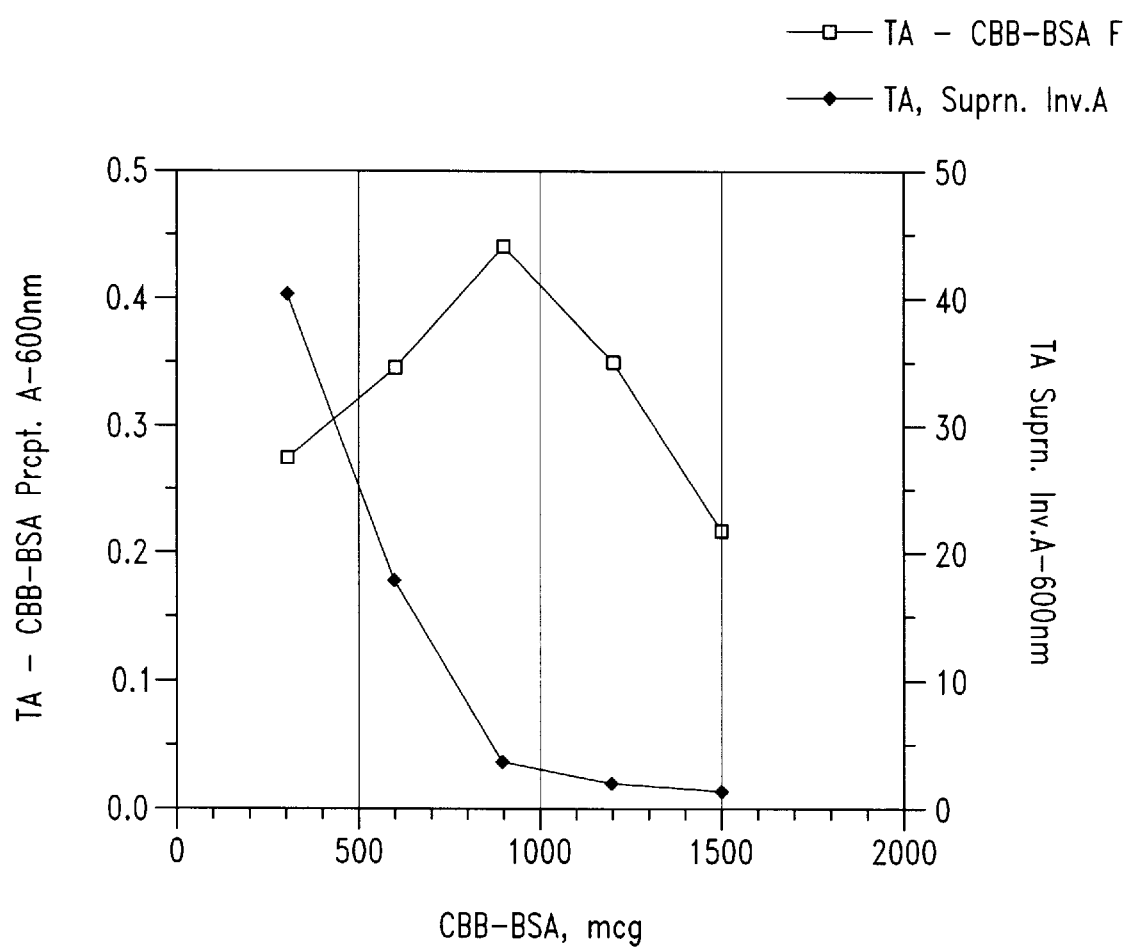
FIG. 8 illustrates that curves determined by empirical measurements are shaped according to theoretical predictions.

FIG. 7 shows theoretical curves plotted for two arbitrary $S_0$ values (100 and 200), and two arbitrary l values (10 and 15). The plots show that the intercept between precipitate absorbance and supernatant inverted absorbance curves is a unique point that is characteristic of the critical number (1), and concentration ($S_0$) of a given substrate. In the practice of the invention, actual, empirically determined intercepts using known values for $N_0$ and $S_0$ could be used to calibrate a standard curve for use in determining the substrate concentration of an unknown sample as mentioned above. FIG. 8 shows that actual empirical measurements match the theoretical curves fairly well.

The curve of the dependence of precipitate absorbance on CBB-BSA concentration has a bell shape character. The position of the maximum of this curve is determined by the following equation:

$$\frac{\partial OD_p}{\partial N_0} = 0 \tag{10}$$

or $$\sum_{k=1} e^{-\overline{m}} \frac{(\overline{m})^k}{k!} - N_0 \frac{\partial \overline{m}}{\partial N_0} \sum_{k=1} e^{-\overline{m}} \frac{(\overline{m})^k}{k!} + \tag{11}$$

$$N_0 \frac{\partial \overline{m}}{\partial N_0} \sum_{k=1} e^{-\overline{m}} \frac{(\overline{m})^{k-1}}{(k-1)!} = 0$$

simple modifications in Equation (11) result in Equation (12):

$$\sum_{k=l} \frac{(\overline{m})^k}{k!} + N_0 \frac{\partial \overline{m}}{\partial N_0} \frac{(\overline{m})^{l-1}}{l-1} = 0 \tag{12}$$

At $K \gg S_0^{-1}$, $(m_{max} N_0)^{-1}$ one has from Equation (3) that $$\overline{m} = \frac{S_0}{N_0}.$$

Equation (12) reduces then to Equation (13):

$$\sum_{k=l} \frac{\left(\frac{S_0}{N_0}\right)^k}{k!} - \frac{\left(\frac{S_0}{N_0}\right)^l}{l-1} = 0 \tag{13}$$

It is seen that the root of the Equation (13) does not depend on the $$\frac{S_0}{N_0}$$

ratio.

Empirical observations of the dependence of the maximum of the curve on tannin concentration indicate that the above relation, $K \gg S_0^{-1}$, $(m_{max} N_0)^{-1}$, is not valid for tannin and/or CBB-BSA concentrations in the ranges studied. In the general case, Equation (3) can be rearranged in the following way:

$$\overline{m} = \frac{m_{max} K N_0 + 1}{2 K N_0} + \frac{1}{2} \frac{S_0}{N_0} - \tag{14}$$

-continued
$$\sqrt{\left(\frac{m_{max} K N_0 + 1}{2 K N_0} + \frac{1}{2} \frac{S_0}{N_0}\right)^2 m_{max} \frac{S_0}{N_0}}$$

Assuming that $$\frac{S_0}{N_0} \ll \overline{m}_{max}, \quad \frac{1}{K N_0}$$

Equation (14) reduces to Equation (15):

$$\overline{m} = \frac{1}{K N_0} \tag{15}$$

As is seen from Equation (12) and Equation (15), in this form, the root of the Equation (12) does not depend on $S_0$, therefore, an increase of $S_0$ will result in the increase of $$\left(\frac{S_0}{N_0}\right)_{max}.$$

The CBB-BSA dye/protein complex of this invention is thus suitable for use in a variety of quantitative assay methods over a wide range of analyte and protein concentrations. The association of the protein with the sensitive chromophore CBB, extends the range of effective dye/protein complex concentrations down to the spectrophotometric limit of detectability of the chromophore.

Figure 9:
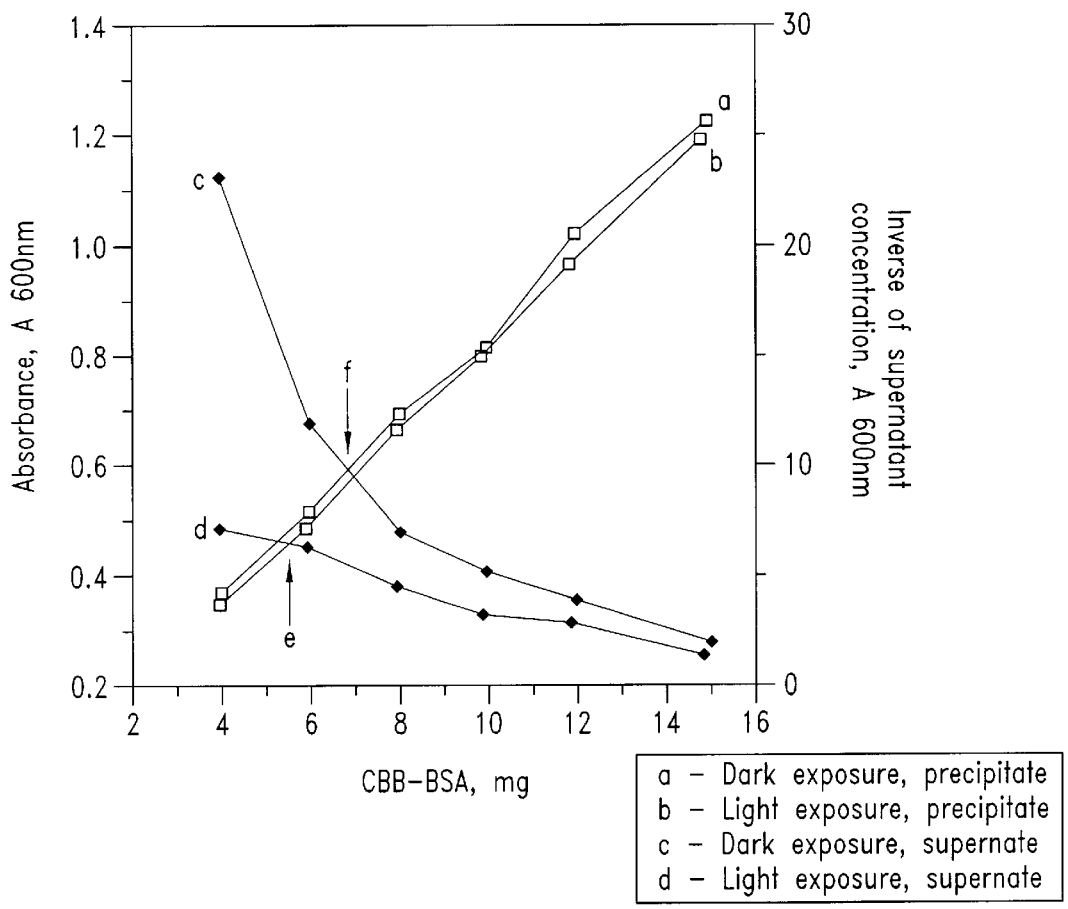
FIG. 9 illustrates the effect of prolonged light exposure on tannin binding properties of the CBB-BSA dye/protein complex.

The chromophore in the CBB-BSA dye/protein complex is stable, but prolonged exposure to light might affect analyte binding properties of the CBB dye/protein complex. Because measurement of the amount of CBB-BSA present in both the supernatant and the precipitate phase is part of a tannin detection method of this invention, it is important to characterize the effects of light on the tannin binding properties of the CBB-BSA dye/protein complex in both phases. The curves shown in FIG. 9 show that prolonged exposure to light (10 hours per day for four weeks) alters the tannin binding properties of the CBB-BSA dye/protein complex. The intercept point for the precipitate (a and b) and inverse supernatant (c and d) curves differ, depending on whether the CBB-BSA dye/protein complex is stored in the dark (a and c) or the light (b and d). The amount of CBB-BSA present in the precipitate does not significantly differ whether the complex is stored in the dark (a) or light (b), however, the amount present in the supernatant increases when CBB-BSA has been exposed to light (d) rather than kept in the dark (c), resulting in a 27% difference in the intercept points (e and f) of the supernatant and precipitate curves. This effect indicates that analyte binding is altered by light exposure of the CBB-BSA dye/protein complex. A practical consequence of this observation to the practice of this invention is that analyte quantification may be altered or not, depending on how the CBB-BSA is stored. Therefore, for a most reliable quantification, either CBB-BSA should be stored in the dark, or more preferably, calibration curves with known samples should be prepared at the same time and with the same batch of CBB-BSA as is used for analyte detection in an unknown sample.

Figure 10:
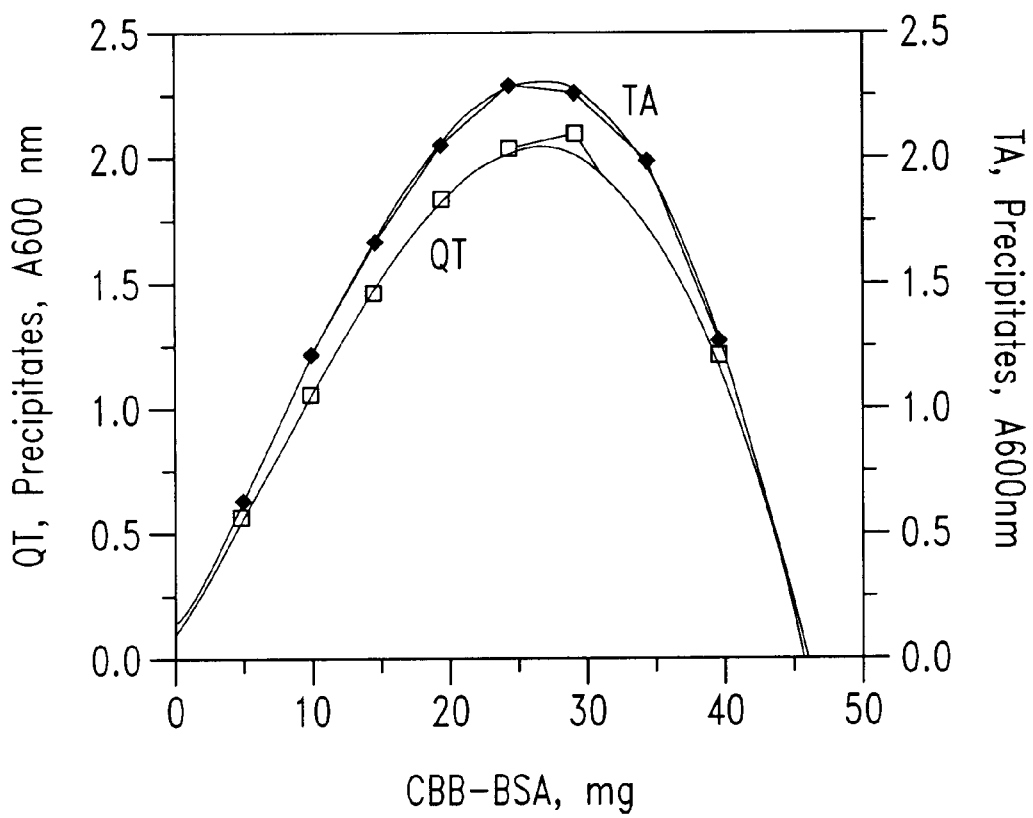
FIG. 10 illustrates differential precipitation of the CBB-BSA dye/protein complex by different tannins.

Another aspect of this invention is a method for the qualitative identification of analytes. The dye to protein ratio at which tannins precipitate differs for different types of tannins because l values differ between tannin species. A result of this property is illustrated in FIG. 10, which shows that the shape of precipitation curves differ for two different tannins—Tannic Acid and Quebraco Tannin. In the identification method, when the concentration of an analyte has been determined by independent means, this invention may be used to identify the analyte species. As shown in FIG. 7, when $S_0$ is the same, but l differs, as may be the case with different tannin species, the resulting intercept between the precipitate and inverse supernatant curves also differs as a function of l. Intercept points can be derived from standard curves prepared from known concentrations of analytes as described above, but additionally, the standards would include known analytes, having different l values. A sample containing a known concentration of an unknown analyte can then be assayed as previously described and compared to the standards for the known analytes. The unknown may then be identified by finding the standard curve representing the l value, and hence the analyte species having the same intercept points.

FIGS. 1 through 4 show properties of the dye/protein complex of this invention while FIGS. 5 through 10 show aspects of a method for quantitative and qualitative detection of analytes using the dye/protein complex, as illustrated by the detection of tannins. The following Table lists several parameters characteristic of the dye protein complex and the tannin detection method of this invention in comparison to those of a previous method that uses BSA covalently labeled with RBB.

TABLE

| Parameter | Previous RBB Method | This Invention |
|---|---|---|
| Dye | Remazol Brilliant Blue | Coomassie Brilliant Blue |
| Chemical origin | Vinlylsulfonyl-anthraquinone | Triphenylmethane sulfonate |
| Water Solubility | 20 mg/ml | 70 mg/ml |
| λmax | 590–620 nm | 582 nm |
| Peak Character at λmax | Broad and shallow | Tall and sharp |
| Extinction coefficient, ε | $0.46 \times 10^4$ L mol$^{-1}$cm$^{-1}$ | $4.5 \times 10^4$ L mol$^{-1}$cm$^{-1}$ |
| Sensitivity, % | 100 | 965 |
| Protein | BSA | BSA |
| Dye/protein reagent | RBB-BSA | CBB-BSA |
| Type of dye/protein reagent | Covalent dye/protein bond | Hydrophobic dye/protein complex |
| λmax | 590 and 620 nm | 602 nm |
| Extinction coefficient, ε | $0.6 \times 10^4$ L mol$^{-1}$cm$^{-1}$ | $5.8 \times 10^4$ L mol$^{-1}$cm$^{-1}$ |
| Dye:protein ratio | 1:13.3 | 1:7.25 |
| Sensitivity, % | 100.0 | 540.4 |
| Dye/protein solubility | | |
| Water | Soluble | Soluble |
| 50% methanol | Precipitates | Soluble |
| Final detection method | Indirect, requires Lowry protein assay | Direct, measures absorbance of precipitate |

The above table illustrates that the tannin detection method of the current invention is superior to previous methods based on using covalently bound RBB-BSA in several respects. The current invention uses a dye, CBB, that has a 9.65 fold greater extinction coefficient than RBB. CBB, has a greater water solubility than RBB. The hydrophobic CBB-BSA dye/protein complex formed by this invention has a 5.4 fold greater extinction coefficient than the covalently bound RBB-BSA reagent. The CBB-BSA dye/protein complex does not precipitate in the presence of high concentrations (50%) of methanol. The CBB-BSA dye/protein complex has a higher dye to protein ratio than the RBB-BSA reagent. The absorbance peak of the CBB-BSA dye/protein complex is narrow compared to the broad peak of the RBB-BSA reagent. The current invention does not require the use of an additional assay for final measurement of the analyte. These differences contribute to a substantially lower cost of making and using the CBB-BSA dye/protein complex relative to the cost of making and using the RBB-BSA reagent.

Other embodiments of the analyte detection method of this invention include, but are not limited to, the detection of specific and non-specific protein binding to ligands, substrates, metabolites and analogues thereof; the detection of antigens that bind to a dye/protein complex comprised of antibodies and vice-a-verse; the detection of proteins that bind to a protein present in the dye/protein complex; assays where the analyte is bound to a solid phase substrate prior to mixing with the dye/protein complex; and assays where the analyte-bound fraction of the dye/protein complex is selectively absorbed from the solution containing the analyte and dye/protein complex.

The following examples are offered by way of illustration, not limitation

EXAMPLES

EXAMPLE 1

PREPARATION OF COOMASSIE BRILLIANT BLUE/BSA COMPLEX

A non-alcoholic, aqueous solution of CBB was prepared by mixing 40 mg of CBB G-250 with 10 ml of 1% w/v NaHCO$_3$, pH 8.2, at room temperature. The mixture was heated in a temperature controlled oven for 3 min at 100° C. The dye quickly and completely dissolved forming a dark-blue dye solution which was cooled to room temperature.

The dye solution was mixed with 300 mg of BSA and vortexed briefly. The mixture was pulse-heated by placing in a temperature controlled oven for another 3 min at 100° C. A stable brilliant-blue color developed. The mixture was cooled by stirring on a magnetic stirrer until the solution reached to room temperature to form a dye/protein mixture containing CBB-BSA.

The dye/protein mixture was dialyzed overnight against 0.2M acetate, pH 5.0, at 4° C. to form a solution containing a dye/protein complex comprised of a CBB-BSA dye/protein complex in a buffer suitable for the detection of tannins by precipitation.

EXAMPLE 2

METHOD FOR USE OF A COOMASSIE BRILLIANT BLUE/BSA COMPLEX FOR THE DETECTION OF TANNINS

A sample of 60 mg dry plant material representing a natural blend of varying amounts (0.1 to 10 mg per gram dry weight) of condensed tannin (e.g., Quebraco tannin) and/or hydrolyzable tannin (e.g., Tannic acid) were extracted in 50% ethanol. A fixed amount of the alcohol extract was mixed in a final volume of 2.5 ml, with increasing amounts of the CBB-BSA dye/protein complex (i.e., 0.2 to 30 mg) prepared as in Example 1. The mixture was briefly vortexed, and incubated overnight at 4° C. to form a precipitate. Standards containing known amounts of Tannic Acid were prepared and treated similarly. The mixtures were centrifuged at 5000× g for 5 minutes and the supernatant and precipitates were separately collected. The precipitates were dissolved in 2.0 ml of 1% sodium dodecyl sulfate (SDS, w/v), and 5% triethanolamine, then diluted 10 fold with 0.2M acetate buffer, pH 5.0. The supernatants were diluted 5 to 10 fold with the 0.2M acetate buffer. Absorbance measurements for both the supernatants and precipitates were made at 602 nm and the inverse of the supernatant absorbance was plotted along with the direct measurement of precipitate absorbance, both as a function of added CBB-BSA is shown in FIG. 8. The intercept of the two plots was determined and compared against the intercept points determined from the standard samples.

EXAMPLE 3

EFFECT OF SDS-TEA ON THE CBB-BSA DYE/PROTEIN COMPLEX

Figure 11:
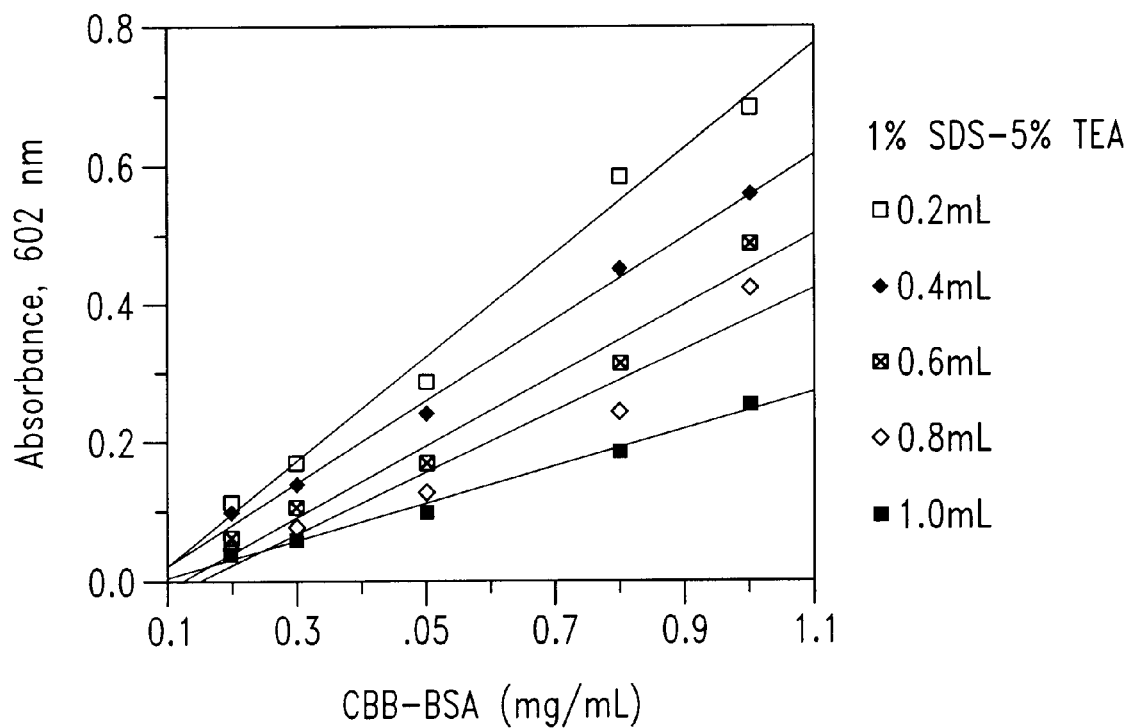
FIG. 11 illustrates a Beers plot of the CBB-BSA dye protein complex after treating with increasing concentrations of detergents.
Figure 12A:
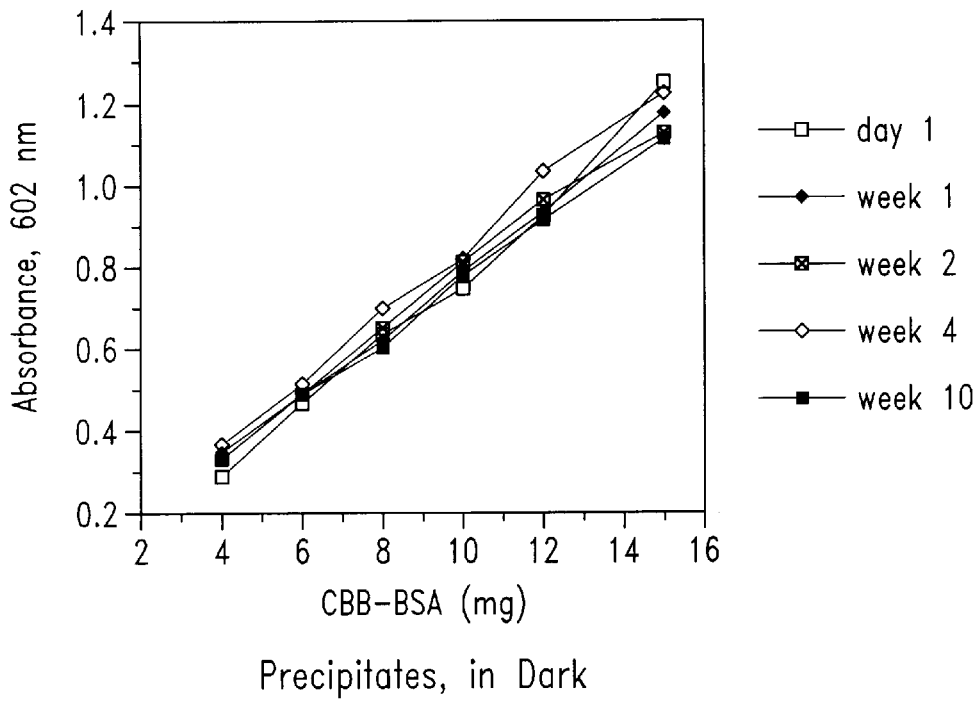
FIG. 12 illustrates the effect of prolonged light exposure on tannin binding properties of the CBB-BSA dye/protein complex.
Figure 12B:
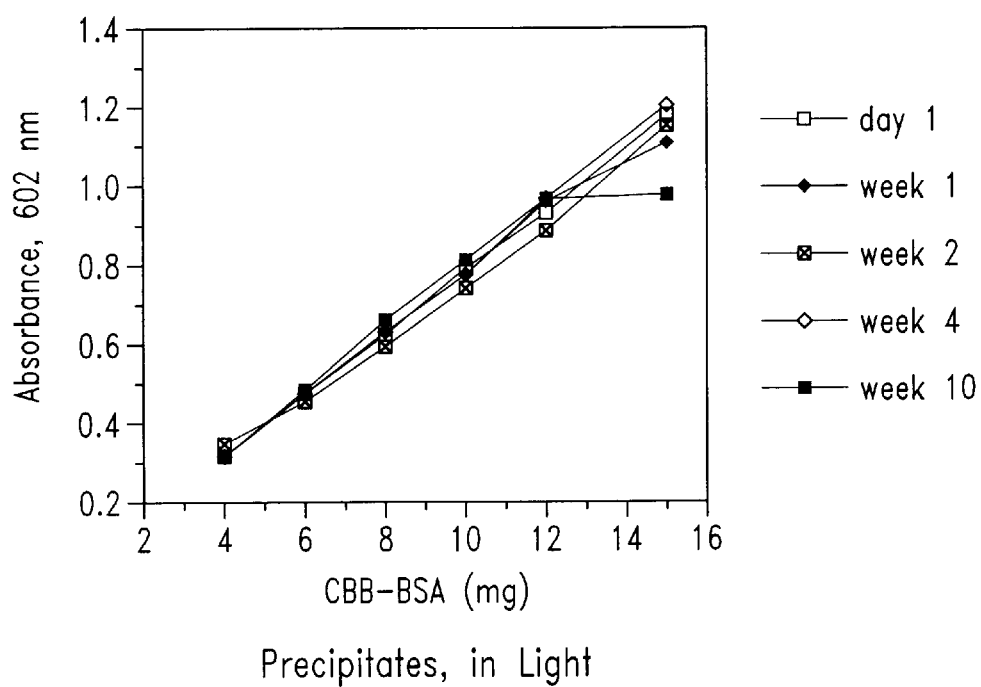
Figure 12C:
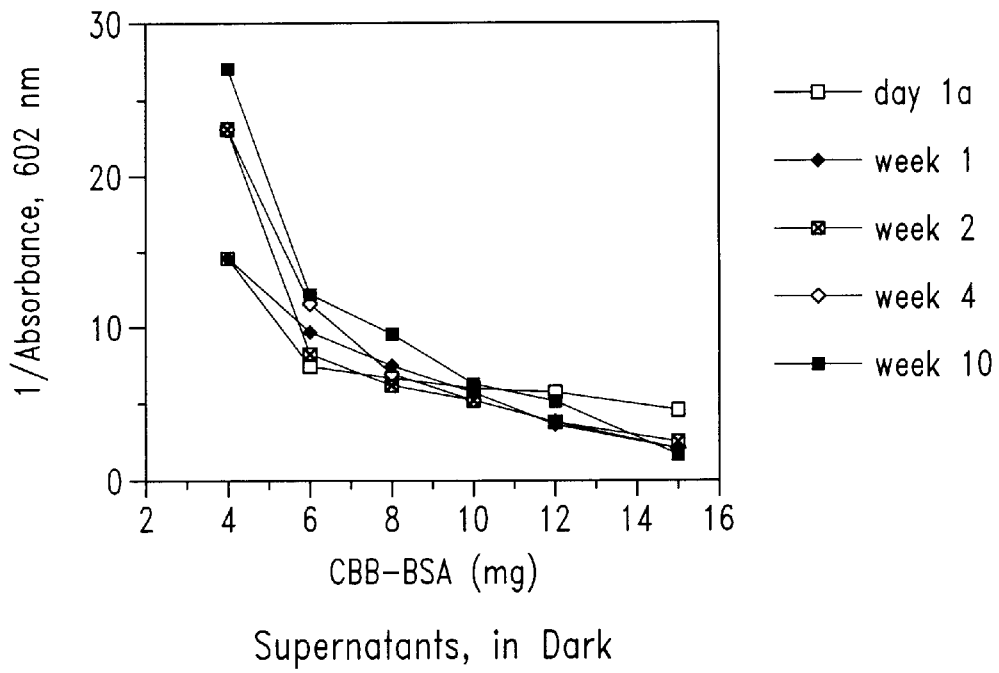
Figure 12D:
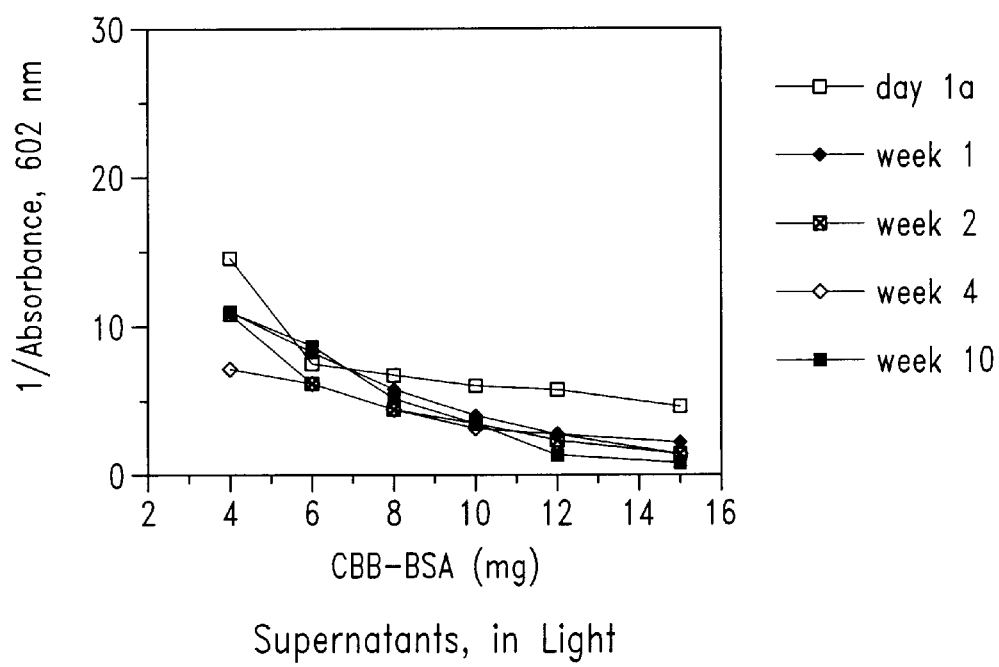

The stability of the anion CBB-BSA dye protein complex to assay conditions containing detergents was investigated. The CBB-BSA material was treated with a mixture of 1% SDS-5% TEA and the Lambert-Beers absorbance characteristics were determined as a function of detergents and CBB-BSA. A set of test-tubes was arranged so that adding increasing volumes of the SDS-TEA mixture incrementally increased the concentration of SDS from 0.2% to 1% but kept constant the amounts of the anion CBB-BSA dye/protein complex. The converse relationship of SDS to CBB-BSA was tested by adding incrementally increased concentrations of the CBB-BSA complex from 0.25 to 1.0 mg ml$^{-1}$ ($3.6\times10^{-3}$M to $1.5\times10^{-2}$M) in the presence of a fixed amount of SDS-TEA so that a curve would be obtained representing the effect of the detergents on the absorbance of the dye/protein complex. FIG. 11 shows that the linearity of the Lambert-Beers absorbance response was not effected by the presence of the detergent but that absolute levels of absorbance was lowered with increasing amounts of detergent. The result indicates that these detergents may lower the sensitivity but not the accuracy of an analyte detection assay so that extraction of samples in the presence of detergents will not obviate the use of the CBB-BSA dye/protein complex as an analyte detection reagent.

EXAMPLE 4

EFFECT OF DARK AND LIGHT STORAGE ON ABSORPTION CHARACTERISTICS OF THE CBB-PSA DYE/PROTEIN COMPLEX

CBB-BSA is a dye chromophore-protein complex. It was important, therefore, to check if light exposure during storage would affect the anion CBB-BSA stability and/or its reliability in detecting and quantifying tannic acid (TA) extracts from plants, food, and feeds. The results from a series of tests (FIG. 8) showed that ten weeks of storage at light or dark did not have noticeable effect on the tannin binding capacity of the CBB-BSA, estimated by the amount of precipitated CBB-BSA / TA complex (FIG. 8, A and B). By contrast, the inverse absorbance of the supernatant in samples exposed to light during 10 weeks, was about ½ of that in samples stored in dark. This difference in the inverse absorbance may be attributed to the higher sensitivity of the dye-protein mixtures stored under light (FIG. 8, C and D).

The practical conclusion from these observations is that a stock preparation of anion CBB-BSA in 0.2M acetate buffer, pH 5.0, can be stored at room temperature or refrigerated at a molar concentration ratio of CBB to BSA as 10.7/1 for at least a month, with no reduction of its stability or bio-assay sensitivity. The refrigeration shelf life of anion CBB-BSA expands to over six months (results not shown). In contrast, prolonged light exposure of anion CBB-BSA prior to assay, may lead to a 50% overestimation of TA content.

EXAMPLE 5

EXPERIMENTAL CALCULATIONS

Strong evidence exist (Atherton et al., 1996; Chial and Splittgerber, 1993; Sohl and Splittgerber, 1991; Compton and Jones, 1985) that most of the dye in the CBB-BSA reaction mixture at higher pH is presented in its deprotonated, anion blue species. Upon this evidence is a simpler model is given in which only the binding of the anion free dye is allowed. The dye-binding analysis is based on the assumption that a binding equilibrium exists between the anion CBB and BSA molecules in solution (Atherton et al., 1996):

anion CBB+BSA⇌anion CBB-BSA (1)

A simple approach based on Lambert-Beer law leads to

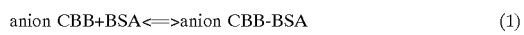

where $\Delta A$ is absorbance change, $\epsilon_B$ and $\epsilon_F$ are molar absorptivities (extinction coefficients), respectively, of the protein-bound dye and free (unbound) dye, while the parameter m is the average number of dye molecules bound per protein molecule at total protein concentration $P_T$. This equation provides a mathematical description of the assay plot, normally a plot of absorbance change upon addition of protein versus protein concentration in the reaction solution.

Under conditions of excess dye, $D_T>>nP_T$, which leads to $D_{Bound}=nP_T$. where Dt equals total concentration of dye and n equals the number of binding sites Equation (2) then becomes $$\Delta A=(\Delta a)nP_T. \quad (3)$$

Under conditions of excess protein, $nP_T>>D_T$, leading to $D_{Bound}=DT$, from which (2) becomes $$\Delta A=(\Delta a)\, D_T. \quad (4)$$

From this model, estimation of both the number of protein dye-binding sites and the association constants for the CBB-BSA complex were carried out from the experimental binding curves.

Figure 13:
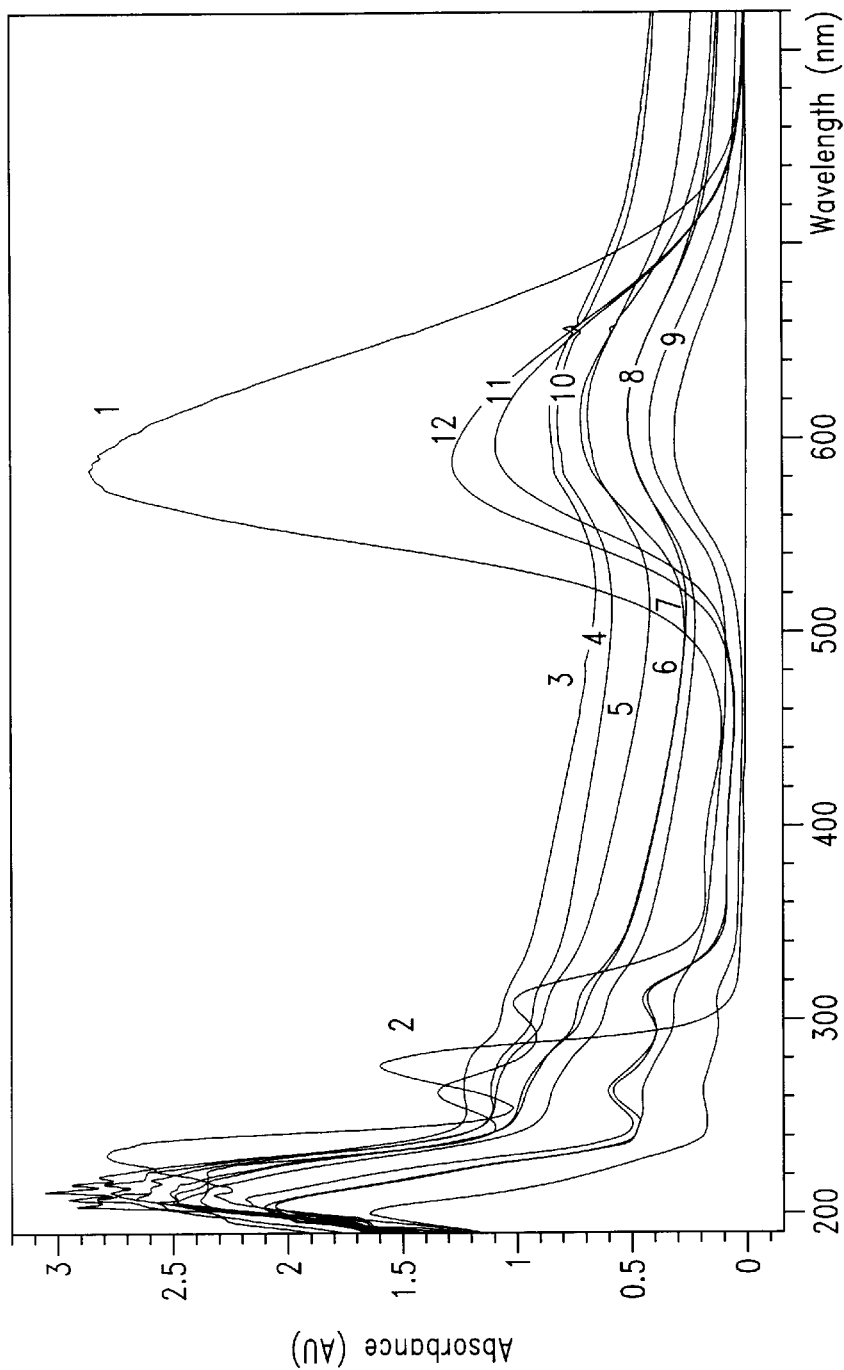
FIG. 13 illustrates a series of spectra curves of mixtures containing the anion CBB dye and BSA in different ratios.
Figure 14:
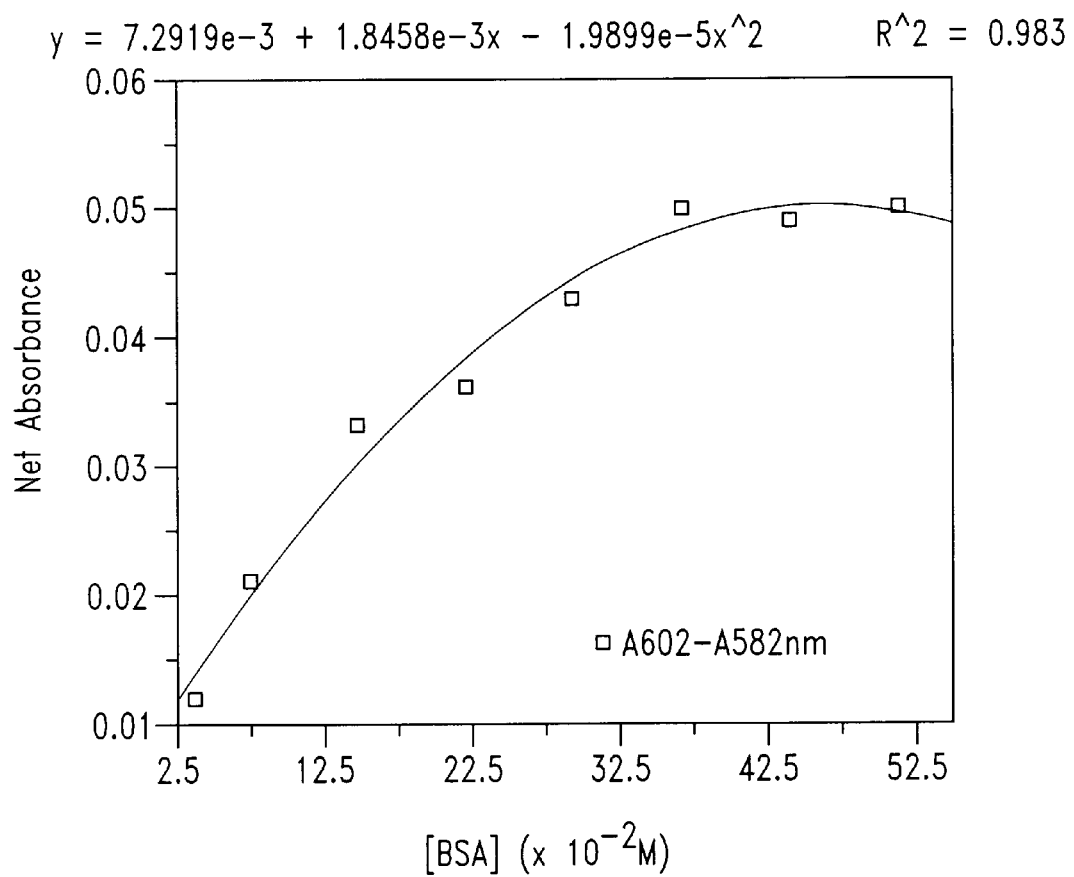
FIG. 14 illustrates net absorbance changes, A602 nm - A582 nm, of CBB-BSA with increase of the molar BSA concentration in a buffered high pH solution.
Figure 15:
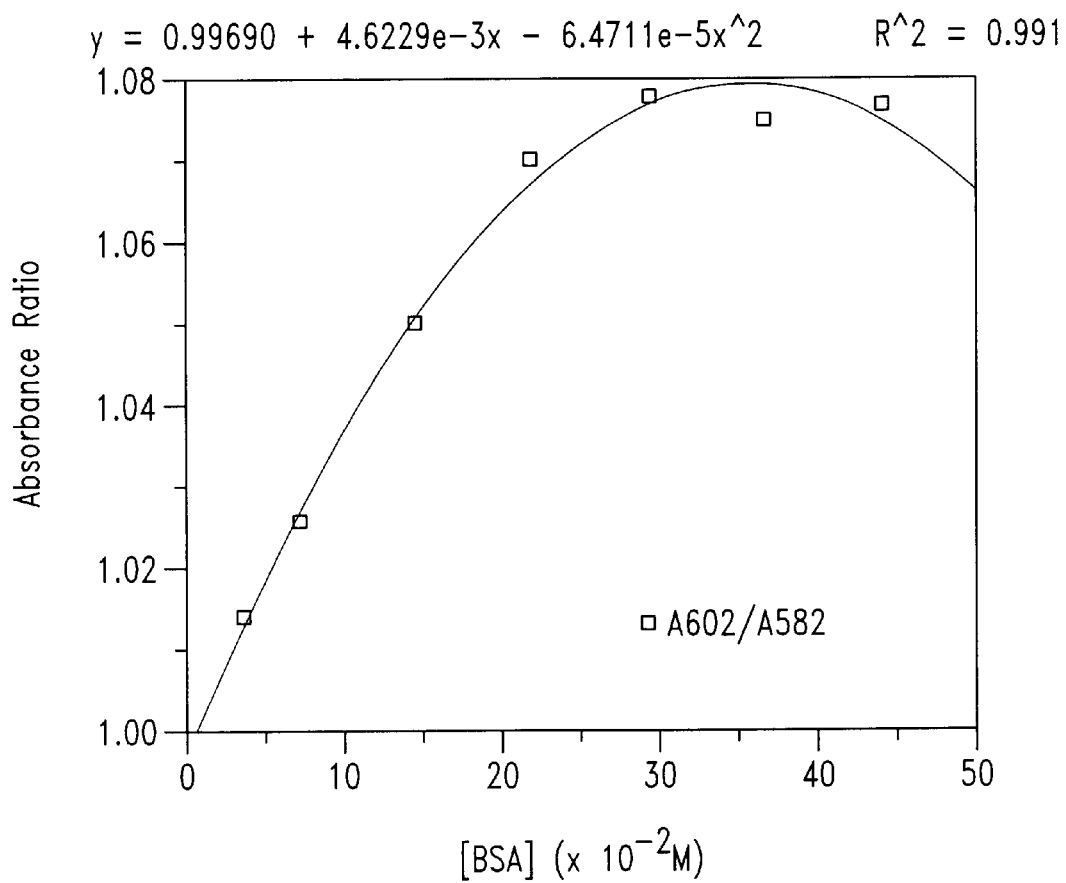
FIG. 15 illustrates a curve plot of dependence of peak absorbances of the anion CBB-BSA at 602 nm over 582 nm on the molar concentration of BSA in a buffered high pH solution.

Experimental binding curves were generated at constant dye levels and upwardly varying protein concentration. FIG. 13 shows a series of spectra for mixtures containing various dye-protein ratios of the anion CBB and BSA prepared at pH>7.0 with subsequent adjustment of the buffered media down to pH 5.0. The experiments were carried out under conditions of high and low dye/protein ratios with constant concentration of the anion free CBB ($6.0\times10^{-5}$M) in all samples.

Where this ratio is reasonably low, all or almost all dye molecules are assumed to be bound to protein, and the peak maximum absorbance at 602 nm is expected to be completely due to the bound dye. With decreased dye/protein ratio in the reaction mixture (curves 3–10), the peak maximum absorbances followed moderate but steady red shift. The samples with high dye/protein ratio (curves 11 and 12) showed further characteristic red shift, almost approaching the peak maximum absorbance for the anion free CBB at 582 nm. In all cases, the net absorbance, A602 nm −A582 nm, which in our experiments reflects the changes of the protein-present absorbance minus zero-protein absorbance, rises as protein concentration increases (FIG. 14). This data is further supported by the curve character, plotted as the dependence of the peak absorbance ratios of 602 nm over 582 nm, on the molar concentration of BSA in buffered high pH solution (FIG. 15). Once again, BSA exhibited a characteristic nonlinear plot during progressive decrease of the CBB/BSA ratio. The slope of the linear portion of the assay curve gives a measure of the sensitivity of the assay, which in our case is equal to 0.00185, i.e., 3.8 times higher, compared to BSA detecting sensitivity of CBB at neutral pH (Atherton et al., 1996; Chial and Splittgerber, 1993).

These curves show that: (i) CBB-BSA binding indeed occurs at the experimental conditions of pH above 7.0, and that at sufficiently high protein levels all dye molecules become bound to protein as indicated by the plateau in absorbance values; (ii) the wavelength of maximum absorbance of the anion free CBB is different from the wavelength maximum absorbance for the anion CBB-BSA complex; (iii) A single dye species predominates in a high pH buffered solution, the blue one. The net absorbance (difference) at 602 nm between free and bound CBB, as well as their molar absorptivities (extinction coefficients) at this wavelength ($\epsilon_{CBB}$=4.5×10$^4$M$^{-1}$cm$^{-1}$ and $\epsilon_{CBB-BSA}$=5.8×10$^4$M$^{-1}$cm$^{-1}$) are sufficient to determine binding of dye to protein under these assay conditions.

Figure 16:
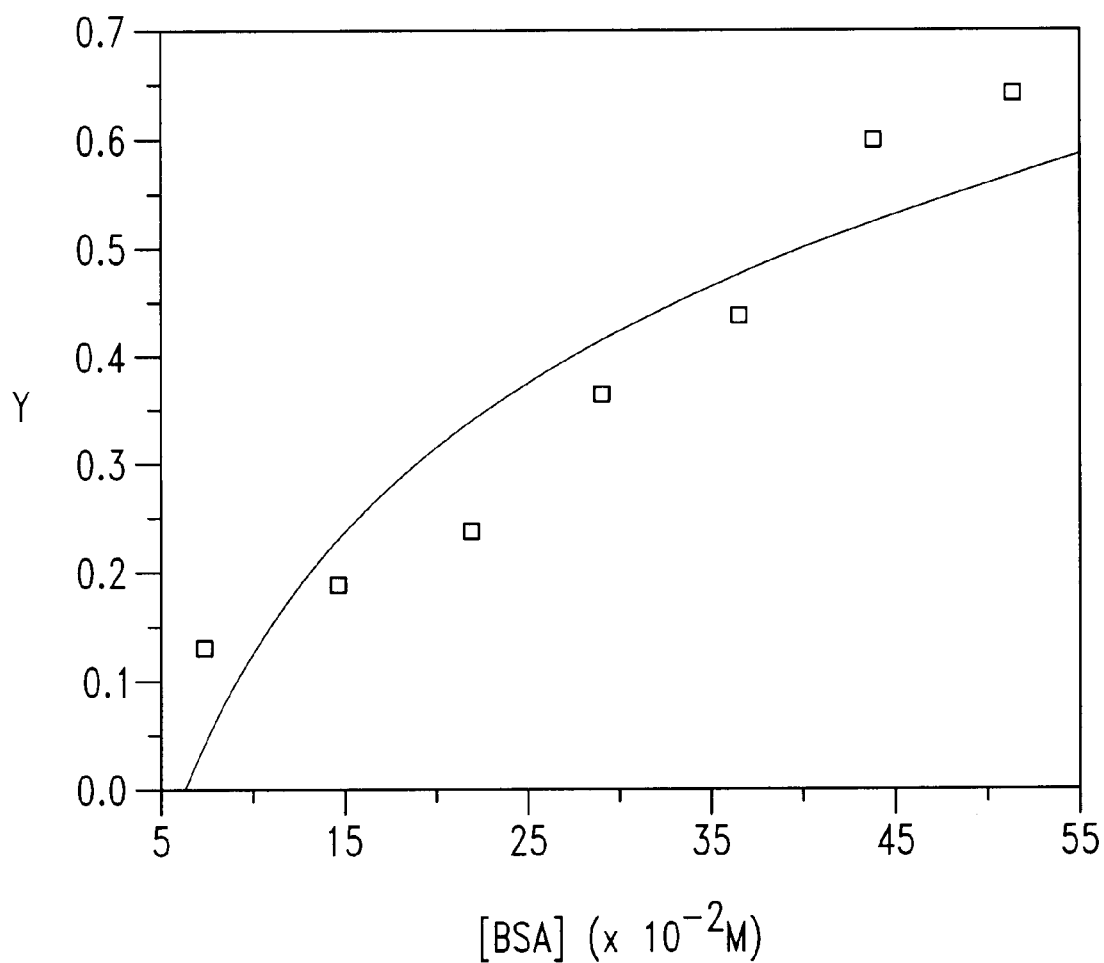
FIG. 16 illustrates the plot of Y versus total protein concentration.

Binding curves are more generally plotted in terms of Y, the fractional saturation of ligand binding sites per protein molecule. When conducting binding studies at constant dye levels, as it is done here, it is convenient to let Y equal the fraction of dye molecules converted to the bound form. The expression for Y then becomes (Sohl and Splittgerber 1991):

$$Y = \frac{\mathcal{E} Abs}{\mathcal{E} Abs_{max}} = \frac{Abs_{sample} - Abs_0}{Abs_{max} - Abs_0} \qquad (5)$$

where $Abs_{sample}$ is the absorbance of a particular protein-dye solution, $Abs_{max}$ is the maximum absorbance observed when sufficient protein is added so that all dye molecules are converted to the protein-bound form, and $Abs_0$ is the zero protein absorbance. Using the Y notation, the binding curve of Y versus total protein concentration was constructed (FIG. 16).

The binding equation

In order to treat the data more efficiently, a general binding equation for any number of binding sites n was derived for the binding curve under conditions of excess protein (Y versus $P_T$, where $P_T$ is total protein concentration). The amount of bound dye is given by:

$$D_T - D_F = \frac{KD_F P_T}{1 + K \cdot D_F} \qquad (6)$$

Division by DT yields the binding equation:

$$\frac{D_T - D_F}{D_T} = Y = \frac{nKD_F(P_T/D_T)}{1 + KDF} \qquad (7)$$

Using the fact that DF/DT=1−Y, the linear form for Y will be:

$$\frac{P_T}{Y} = \frac{1}{nK}\left[\frac{1}{1-Y}\right] + \frac{D_T}{n} \qquad (8)$$

Figure 17:
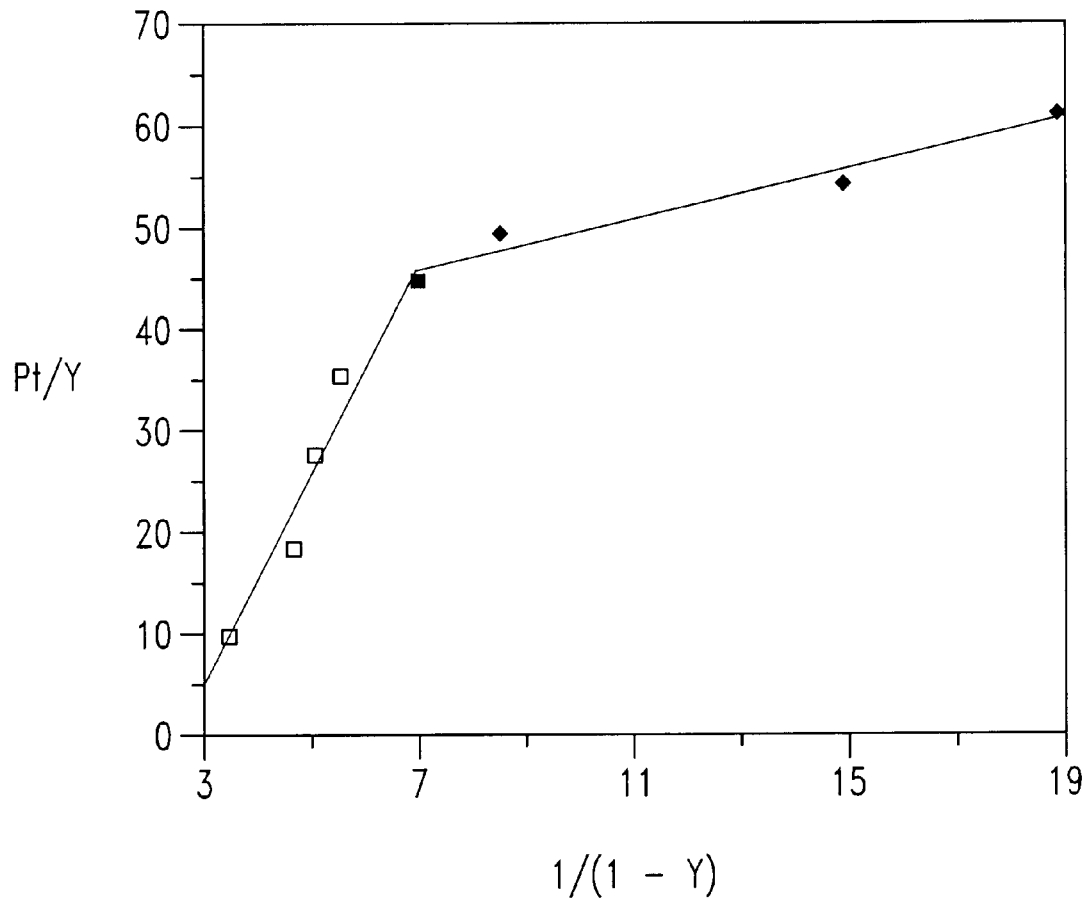
FIG. 17 illustrates the Scatchard binding plot.

This form allows the most useful plots of the binding data, i.e., straight line plots such as Scatchard plots (Scatchard, 1949). The constants n and K are evaluated from the slopes and intercepts of the dependence of PT/Y on 1/1−Y, provided that a linear relationship is obtained (FIG. 17).

In the case where various binding sites on the protein have different binding affinities (McManus et al., 1981; Van Buren and Robinson, 1969), or are interacting, one expects a nonlinear dependence of PT/Y on 1/1−Y. Our analysis shows that the experimental dependence of PT/Y on 1/1−Y for the anion CBB binding by BSA does not fit Equation 8. Specifically, increasing the dye/protein ratio resulted in an apparent increase in the value of n, and a decrease in K.

The assay sensitivity, given by the slope of the assay plot, depends on the magnitude of the molar absorptivity difference between free and bound dye and also on the number of dye molecules bound per protein molecule under assay conditions. When the protein molecule is saturated with dye, m becomes equal to n, the total number of binding sites.

Binding of the CBB molecules to BSA molecules is assumed to occur randomly, so that at a given total dye/protein ratio, individual protein molecules will contain differing numbers of bound dye. Assuming a Poisson type distribution (J(k)) of CBB bound to BSA, i.e., $$J(k) = e^{-m}\frac{(m)^k}{K!} \qquad (9)$$

the amount of CBB-BSA complexes in solution (Cs) is given by:

$$C_s = P_T \times \sum_{k=1} J(k) = P_T \times \sum_{k=1} e^{-m}\frac{(m)^k}{K!} \qquad (10)$$

If each protein molecule has n identical noninteracting sites for dye molecules, one has from the mass action law:

$$m = n\frac{K \times r \times D_F}{1 + K \times r \times D_F} = n\frac{K(rD_T - mP_T)}{1 + K(rD_T - mP_T)} \qquad (11)$$

where K is the equilibrium binding constant, r is the number of binding sites on the protein molecule that can be occupied by one dye molecule, $D^F$ and $D^T$ are the concentrations of free (unbound) and of the total (bound and unbound) dye, and $P^T$ is the total concentration of protein.

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

We claim:

1. A method for forming a hydrophobically associated, Coomassie Brilliant Blue (CBB) dye/protein complex, comprising the step of pulse heating a protein in a first aqueous solution to a first temperature for a pulse period, then cooling to a second temperature to form a solution containing the CBB dye/protein complex, wherein the first aqueous solution contains CBB and has a pH greater than 4.0, and with the proviso that the first aqueous solution does not contain an alcohol.

2. A method for forming a hydrophobically associated, CBB dye/protein complex, comprising the steps of:
   pulse heating a protein in a first aqueous solution to a first temperature for a pulse period, then cooling to a second temperature to form a solution containing a CBB dye/protein mixture; and
   dialyzing the CBB dye/protein mixture against a second aqueous solution having a pH greater than 4.0, to obtain the CBB dye/protein complex, with the proviso that neither of the first or the second aqueous solutions contain an alcohol.

3. The method of claim 2 wherein the first aqueous solution is prepared by pulse heating the dye to a temperature of about 100° C. then cooling to room temperature.

4. The method of any one of claims 1–3 wherein CBB is CBB G-250.

5. The method of claim 4 wherein the protein is bovine serum albumin (BSA).

6. The method of claim 4 wherein the protein is selected from enzymes, lectins, antibodies, antigens, binding proteins, peptide hormones, transport proteins and receptors.

7. A CBB dye/protein complex prepared according to the method of any one of claims 1–6.

8. A method for detecting tannins, comprising the steps of:
mixing a sample containing tannins with a solution having a pH greater than 4.0. and containing a CBB-BSA dye/protein complex to form a precipitate containing a tannin-bound CBB-BSA dye/protein complex; and
dissolving the precipitate in an aqueous solvent and measuring a spectral absorbance of the dissolved precipitate.

9. A method for detecting tannins, comprising the steps of:
mixing a sample containing tannins with a solution having a pH greater than 4.0 and containing a CBB-BSA dye/protein complex to form a precipitate containing a tannin-bound CBB-BSA dye/protein complex and a supernatant; and
dissolving the precipitate in an aqueous solvent and measuring a spectral absorbance of the dissolved precipitate and the supernatant.

10. A method for detecting an analyte that binds to a CBB dye/protein complex, comprising the steps of:
mixing a sample containing the analyte with a solution having a pH greater than 4.0 and containing the CBB dye/protein complex to form a mixture containing an analyte-bound fraction and an unbound fraction of the CBB dye/protein complex; and
detecting the analyte by assaying the CBB dye/protein complex present in at least one of the analyte-bound fraction or the unbound fraction.

11. The method of claim 10 wherein detecting the analyte is accomplished by measuring a spectral absorbance of a precipitate or a supernatant containing the CBB dye/protein complex.

12. The method of claim 10 wherein detecting the analyte is accomplished by measuring a spectral absorbance of the solution containing the CBB dye/protein complex before and after mixing with the analyte.

13. The method of claim 10 wherein detecting the analyte is accomplished by adsorption of the analyte-bound fraction of the CBB dye/protein complex onto a solid phase substrate followed by scoring for the presence or amount of the CBB dye/protein complex present on the solid substrate after washing the unbound fraction from the solid phase substrate.

14. The method of claim 10 wherein the sample containing the analyte is attached to a solid phase substrate prior to mixing with the solution containing the CBB dye/protein complex, and detecting the analyte bound fraction is accomplished by scoring for the presence or amount of the CBB dye/protein complex present on the solid substrate after washing the unbound fraction from the solid phase substrate.

15. The method according to any one of claims 1–6 wherein the first aqueous solution has a pH of 7.0 or greater.

* * * * *

UNITED STATES PATENT AND TRADEMARK OFFICE
CERTIFICATE OF CORRECTION

PATENT NO : 6,057,160
DATED : May 2, 2000
INVENTOR(S) : Silber et al.

It is certified that errors appear in the above-identified patent and that said Letters Patent are hereby corrected as shown below:

Column 2, line 39, "proteins-straining" should read --protein-straining--.

Column 3, line 33, "for maling" should read --for making--.

Column 8, line 55, "H 5.0" should read --pH 5.0--.

Column 16, line 57, "50% ethanol" should read --50% methanol--.

Column 17, line 46, "CBB-PSA DYE" should read --CBB-BSA DYE--.

Column 20, line 38, "$D^F$" should read --$D_F$--.

Column 20, line 38, "$D^T$" should read --$D_T$--.

Column 20, line 40, "$P^T$" should read --$P_T$--.

Figure 3, y axis label, "Absorbance, A600nm" should read --Absorbance, A602nm--.

Figure 4, y axis label, "Absorbance, A600nm" should read --Absorbance, A602nm--.

Figure 5, y axis label (right side), "A600nm" should read --A602nm--.

Figure 6, y axis label, "Absorbance, A600nm" should read --Absorbance, A602nm--.

Figure 8, y axis label (right side), "TA-CBB-BSA Prcpt. A-600nm" should read --TA-CBB-BSA Prcpt. A-602nm--.

Figure 8, y axis label (left side), "TA Suprn. Inv.A-600nm" should read --TA Suprn. Inv.A-602nm--.

Figure 9, y axis label (right side), "Absorbance, A 600nm" should read --Absorbance, A 602nm--.

UNITED STATES PATENT AND TRADEMARK OFFICE
CERTIFICATE OF CORRECTION

PATENT NO. : 6,057,160

DATED : May 2, 2000

INVENTOR(S) : Silber et al.

It is certified that error appears in the above-identified patent and that said Letters Patent is hereby corrected as shown below:

Figure 9, y axis label (left side), "Inverse of supernatant concentration, A 600nm" should read --Inverse of supernatant concentration, A 602nm--.

Figure 10, y axis label (right side), "QT, Precipitates, A600nm" should read --QT, Precipitates, A602nm--.

Figure 10, y axis label (left side), "TA, Precipitates, A600nm" should read --TA, Precipitates, A602nm--.

Column 10, line 27, "measured at 600nm" should read --measured at 602nm--.

Signed and Sealed this

Fifteenth Day of May, 2001

Attest:

NICHOLAS P. GODICI

*Attesting Officer*    *Acting Director of the United States Patent and Trademark Office*